United States Patent [19]
Hoyt et al.

[11] Patent Number: 5,943,129
[45] Date of Patent: Aug. 24, 1999

[54] FLUORESCENCE IMAGING SYSTEM

[75] Inventors: Clifford C. Hoyt, Needham; Peter J. Miller, Somerville, both of Mass.

[73] Assignee: Cambridge Research & Instrumentation Inc., Cambridge, Mass.

[21] Appl. No.: 08/906,665

[22] Filed: Aug. 7, 1997

[51] Int. Cl.$^6$ .................................................. G01N 21/64
[52] U.S. Cl. ...................... 356/318; 356/417; 250/458.1
[58] Field of Search ................................... 356/317, 318, 356/417; 250/458.1, 459.1, 461.1, 461.2

[56] References Cited

U.S. PATENT DOCUMENTS

| | | |
|---|---|---|
| 3,705,755 | 12/1972 | Baer . |
| 3,785,714 | 1/1974 | Hock et al. . |
| 3,860,813 | 1/1975 | Herzog et al. . |
| 4,122,348 | 10/1978 | Bruck . |
| 4,621,911 | 11/1986 | Lanni et al. . |
| 5,218,195 | 6/1993 | Hakamata . |
| 5,323,009 | 6/1994 | Harris . |
| 5,386,112 | 1/1995 | Dixon . |
| 5,394,268 | 2/1995 | Lanni et al. . |
| 5,457,536 | 10/1995 | Kornfield et al. . |
| 5,477,321 | 12/1995 | Johnson . |
| 5,521,705 | 5/1996 | Oldenbourg et al. . |
| 5,521,755 | 5/1996 | Stankewitz . |
| 5,610,765 | 3/1997 | Colucci . |
| 5,672,880 | 9/1997 | Kain ...................................... 356/458.1 |
| 5,719,391 | 2/1998 | Kain ...................................... 250/458.1 |

OTHER PUBLICATIONS

"Synthesis of Optical Birefrigerent Networks", Progress in Optics IX (North–Holland Amerstand) 1971, pp. 123–177 by E.O. Amman.

"Flat Passband Birefrigerent Wavelength Domain Multiplexer", Electronics Letters 23(3), 106–7 (1987) by W.J. Carlsen and C.F. Buhrer.

"Optical Network Synthesis Using Birefrigerent Crystals. I. Synthesis of Lossless Networks of Equal–Length Crystals", J. Opt. Soc. Am. 54, 1267 (1264) by S.E. Harris, E.O. Amman and C. Chang.

*Primary Examiner*—F. L. Evans
*Attorney, Agent, or Firm*—Cohen, Potani, Lieberman & Pavane

[57] ABSTRACT

A fluorescence imaging system for epi-illumination wherein the usual dichroic beamsplitter is replaced by a polarizing beamsplitter (PBS). The sample is excited with light that is linearly polarized to a significant degree, and fluorescent emission light is collected in the orthogonal linear polarization state. Excitation light that is scattered or reflected by the sample is rejected by the PBS, while the desired emission light is captured for imaging by a detector. By eliminating the usual dichroic beamsplitter member, the imaging system removes the barriers to multi-spectral imaging that such members conventionally impose. A wavelength-selective birefringent network may also be interposed between the beamsplitter and the sample for converting the polarization of either the excitation or the emission light to the orthogonal state without defeating this desirable rejection property, thus permitting measurement of the sample emissions in either or both linear polarization states for assessing fluorescence polarization.

28 Claims, 17 Drawing Sheets

FLUORESCENCE IMAGING SYSTEM

BACKGROUND OF THE INVENTION

The present invention is directed to a fluorescent imaging system.

There are currently numerous methods for fluorescent imaging, all of which have as their objective the illumination of a sample with excitation light of one wavelength while imaging a resulting fluorescent emission at a second, longer wavelength. Because the fluorescent efficiency of many samples is low, i.e. typically 1 photon of fluorescent emission or less per 100 photons of excitation, the optical imaging system must efficiently collect the weak fluorescent emission without interference from the much stronger excitation signal. The optical system must provide an efficient optical path for delivering emission light to the image, but little or no such path for excitation light. Typically, spectral filters, such as colored-glass or interference filters, are used to provide at least some degree of the required wavelength selectivity which is enhanced through a careful choice of the overall optical design.

Prior art optical systems normally incorporate one optical path for the excitation light and a second optical path for the fluorescent emission. These optical paths necessarily overlap at the sample, and in many systems the two paths also make common use of one or more of the optical elements.

Two approaches are widely used to minimize the coupling of light from the excitation to the emission optical path. The first approach is to illuminate the sample with light having a range of angles to which the emission optics are non-responsive. One method for achieving this is illuminating the sample from the side while collecting the fluorescent emission from the top. A portion of the fluorescent emission, which is more or less isotropic in angular distribution, is captured by the collection optics while the angularly-restricted excitation beam leaving the sample proceeds, uncollected, to a baffled optical trap.

Although such an arrangement can be used successfully for single-point measurements, it is not generally suitable in imaging applications. Imaging systems commonly use "dark-field" illumination, in which diaphragms, or zone plates, in the illumination and collection objectives insure that the sample is illuminated over a first selected cone of angles while the emission is collected over a second, but different, cone of angles. An inherent feature of the dark-field method is that the effective numerical aperture ("NA") of the objectives is reduced, causing a significant and undesired reduction in optical efficiency. Moreover, by reducing the NA the diffraction limit of the instrument is degraded so that both image quality and resolution also deteriorate.

The second known approach to minimizing coupling of light from the excitation to the emission path is separating those two optical paths through the use of a dichroic beamsplitter. Most widely employed is the "epi-illumination" method, which utilizes a dichroic beamsplitter that strongly reflects light at the excitation wavelength, but transmits light at the emission wavelength. The beamsplitter is oriented to reflect light from the illumination optics into a common objective through which it illuminates the sample. Fluorescent emission, collected by the same objective, passes through the dichroic beamsplitter without significant loss and proceeds along the remainder of the emission optical path. Since the beamsplitter provides low transmission at the excitation wavelength, little of the stray excitation light that is reflected or scattered by the sample finds its way into the emission optical path. Unlike the dark-field arrangement, there are no limitations on the NA of the objective, and it is possible to use objectives with a high NA to achieve high throughput and high image resolution.

However, in the epi-illumination method the dichroic beamsplitter inherently restricts one to a single set of excitation and emission wavelengths since the beamsplitter affords high reflection at a particular predetermined band of excitation wavelengths and high transmission at another particular predetermined band of emission wavelengths.

While it is possible to design a dichroic beamsplitter which provides for three or even four excitation bands and a corresponding number of emission bands, for several reasons such beamsplitters offer only a limited increase in versatility. First, the optical performance of a multi-band device is generally inferior to that of a single-band device due to limitations in the optical coating art. Second, the wavelengths of the various bands cannot be independently specified or selected due to constraints in the thin-film coating art. However, each particular fluorescent species has a spectral response which dictates the use of an optimal band for excitation and, accordingly, an optimal emission band. In practice, the various bands reflected and passed by the beamsplitter cannot all be chosen for maximum efficiency of excitation and collection, with the result that for one or more fluorescent species, the system is inefficient at the excitation fluorescence and/or at the fluorescent emission signal wavelengths.

A third drawback of multiband beamsplitters is that any given wavelength must be dedicated to either excitation or to emission. If dedicated to excitation, the dichroic beamsplitter must be highly reflective, whereas for emissions it must be highly transmissive. Thus, it is fundamentally impossible with a dichroic beamsplitter to observe fluorescent emission at any wavelength which is or may be used as an excitation band. This presents a severe restriction in attempts to devise a system for imaging multiple fluorescent species. It is undesirable to mechanically exchange the beamsplitter to overcome this restriction because this leads to vibration and image shift in the system.

In addition, the restrictions imposed by a dichroic beamsplitter severely restrict spectroscopic imaging systems. When more than one fluorescent species is present, the emission spectra may overlap and the observations at a single wavelength may not uniquely identify the emitting species. By taking a complete spectrum and resolving it into relative contributions from the different species, each of which has a characteristic spectral shape, the presence and quantity of each species can be accurately determined. However, this requires a fluorescence imaging system to obtain a spectrum at many wavelengths. Although it is ideally desirable to accommodate a continuous unbroken spectrum over the full range of emission, such an objective is not achievable by the use of a dichroic beamsplitter which merely dedicates specific fixed wavelength bands to excitation and others to emission.

Thus, there is currently no fluorescent imaging system that accommodates the use of high and unrestricted NA in the objectives and which does not impose severe limits on the spectral location of the excitation and emission bands that are employed for imaging multiple fluorescent species, or from spectroscopic imaging of fluorescent species.

SUMMARY OF THE INVENTION

It is accordingly an object of the present invention to provide a fluorescent imaging system that can be used with many fluorescent species and which permits dense and even overlapping spectral bands to be employed for excitation and emission. The invention overcomes the limitations imposed by multiband dichroic beamsplitters, and eliminates the need for interchanging simple dichroic beamsplitters when imaging multiple fluorescent species. The present invention further provides a system with no moving parts for measuring fluorescent polarization with the option of using several excitation and emission bands.

The invention is more particularly directed to a fluorescent imaging system in which the normal dichroic beamsplitter is replaced by a polarizing beamsplitter (PBS). The fluorescent imaging system of the invention includes an illumination source that provides a beam of optical radiation along an optical path. A PBS element, which selectively reflects or transmits optical radiation differentially based on its polarization state, is disposed in the optical path. The optical radiation is at least predominantly in a first polarization state leaving the PBS element and may contain a small amount of light orthogonal to the first polarization state, and is directed from the PBS toward a location at which the sample being observed is located. The emissions from the sample pass through the PBS element and, by selective reflection or refraction in the PBS element, are selected to be substantially of the orthogonal polarization state to the first polarization state. The system additionally includes a detector that is responsive to, and is disposed to receive, fluorescent emissions from the sample.

The illumination optics generate light that is linearly polarized in a state for which the PBS is highly reflective. Fluorescent emissions having the orthogonal polarization state, for which the PBS is transmissive, are collected and used to form an image of the sample fluorescence. Reflected excitation light having the same polarization state for which the PBS is highly reflective is rejected by the PBS and thus proceeds no further along the emission optical path. The present invention accordingly provides a high degree of selectivity between the excitation and emission light, without the restrictions on NA that are imposed by dark-field systems.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, wherein like reference characters denote similar elements throughout the several views.

DESCRIPTION OF THE PREFERRED EMBODIMENT

Figure 1:
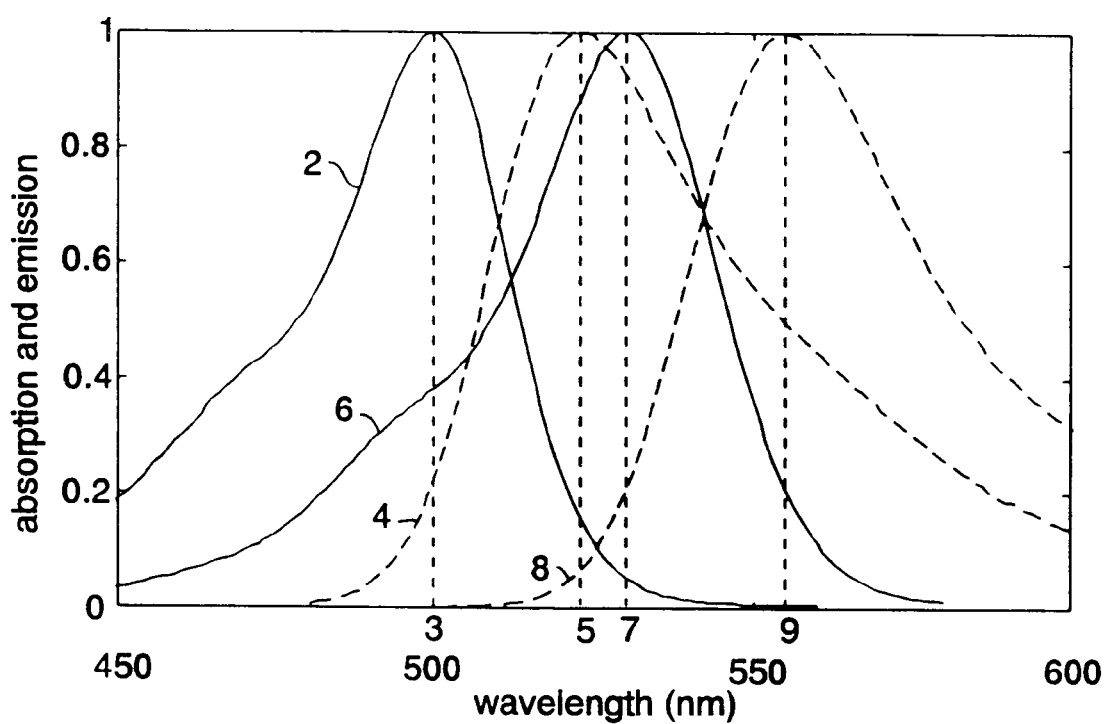
FIG. 1 graphically depicts the absorption and emission spectra for two fluorescent species.

Referring initially to FIG. 1, a first sample species has an absorption spectrum (curve 2) with maximum absorption at a wavelength identified as a spectral feature 3 and an emission spectrum, depicted by curve 4, when excited at the wavelength 3. The emission spectrum 4 shows a maximum near the wavelength identified as 5. A second species has an absorption spectrum (curve 6) with maximum absorption at a wavelength identified as spectral feature 7. When excited at the wavelength 7, the emission spectrum is shown by curve 8; this emission has a maximum at about a wavelength identified as 9.

Figure 2:
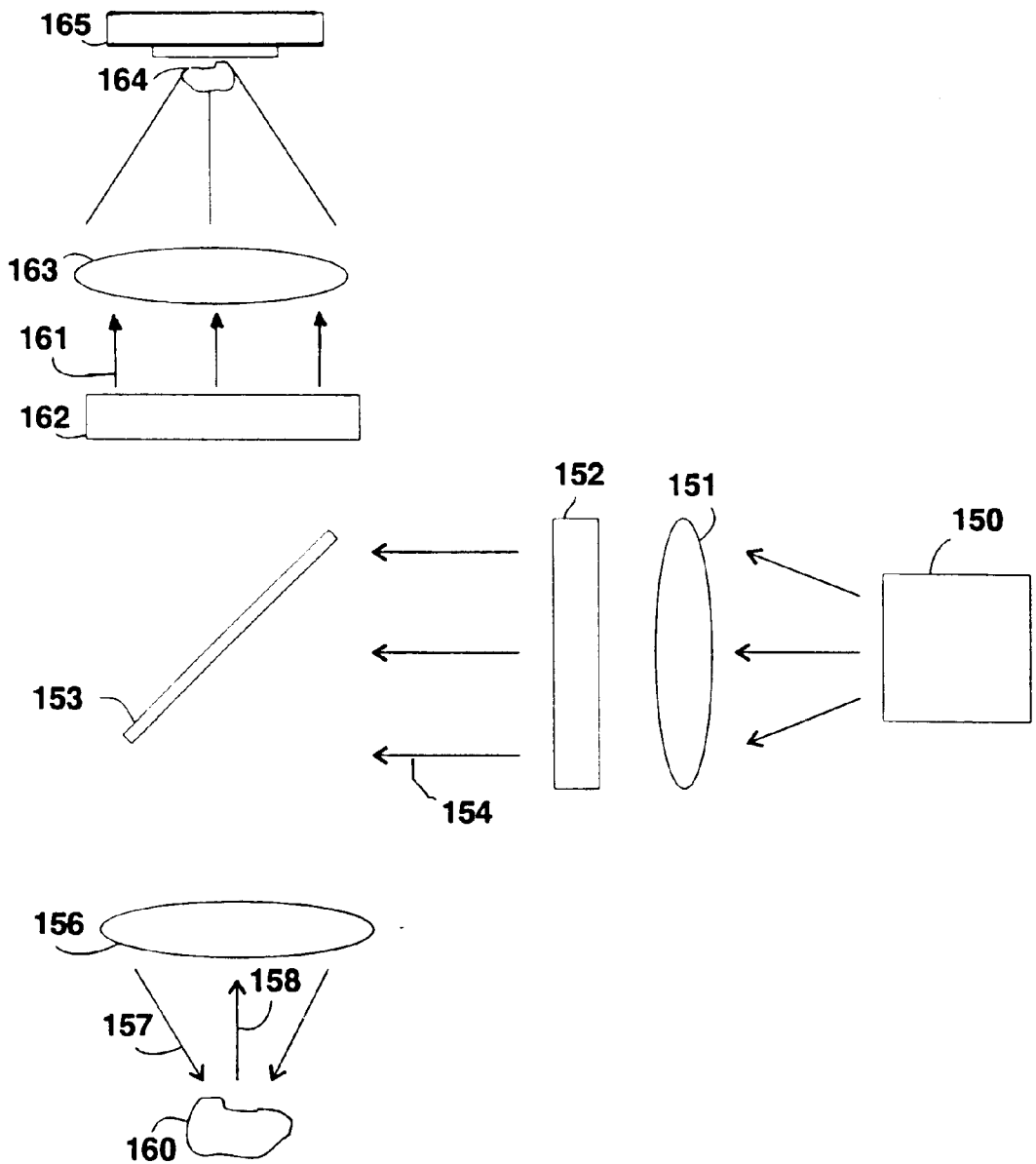
FIG. 2 diagrammatically illustrates a prior-art epi-illuminated system for fluorescent imaging.

FIG. 2 depicts a prior art fluorescent imaging system. Light from an illumination source 150 passes through associated illumination optics 151 and then to a first spectral filter 152. Filter 152 transmits light 154 of a selected spectral range to excite fluorescence. Excitation light 154 proceeds to a dichroic beamsplitter 153 that reflects the light 154 toward objective 156, at which the rays 157 are focused on a sample 160. Fluorescent emission 158 from the sample is gathered by the objective 156 and passes through dichroic member 153 to a second spectral filter 162 that transmits light 161 within a selected spectral range. Image-forming optics 163 form an image 164 of the fluorescent emission upon a detector 165.

Figure 3:
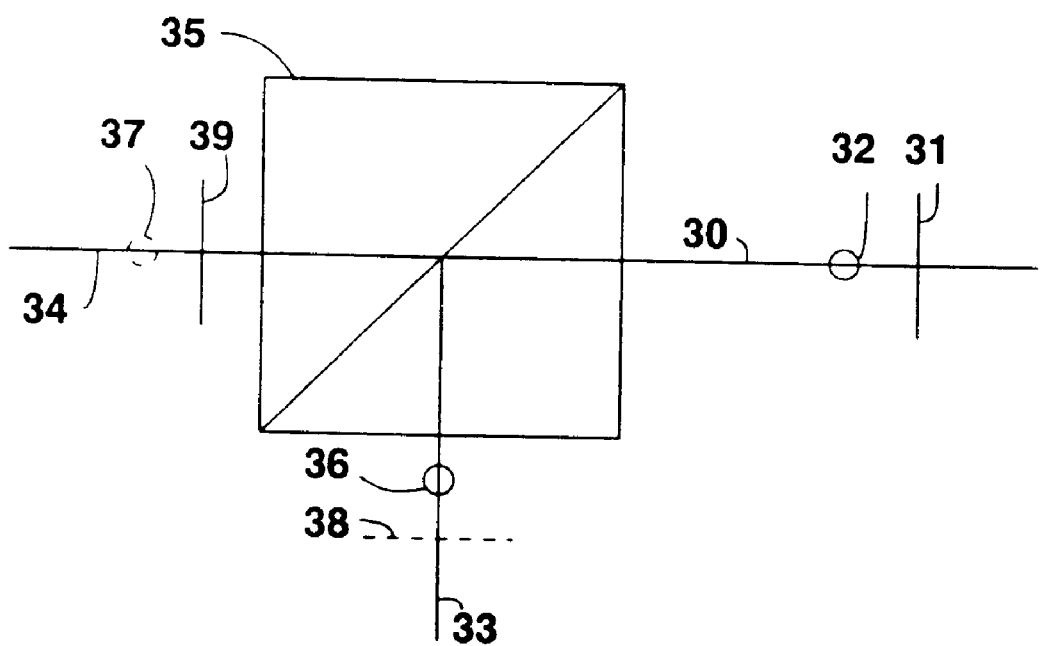
FIG. 3 depicts the properties of a polarizing beamsplitter (PBS)

FIG. 3 illustrates the properties of a polarizing beamsplitter (PBS) element; the figure presents a side-view in which all rays (except as otherwise indicated) lie in the plane of the drawing. As shown in FIG. 3, a beam of light 30 is incident on a PBS 35. The beam 30 consists of optical radiation having a polarization mode 31 with an E-field in the plane of the drawing, and a polarization mode 32 having an E-field perpendicular to the plane of the drawing. By convention, components 31 and 32 are respectively referred to herein as the P component and the S component. At PBS element 35, the S component 32 is substantially reflected and becomes component 36 of beam 33 with a polarization E-field that remains perpendicular to the plane of the drawing. A weak component is transmitted by the PBS 35 and becomes component 37 of a beam 34. Conversely, the P-component 31 is substantially transmitted through PBS 35, and only a weak portion is reflected to form component 38 of beam 33 having an E-field in the plane of the drawing; the major portion of P-component 31 is transmitted through PBS 35 and becomes component 39 of beam 34. Although the PBS is shown as a cube with its hypotenuse at a 45° angle to the incident beam 30, the PBS may alternatively comprise a plate-type or reflective polarizing film-type PBS device and nevertheless operate in a similar fashion. In addition, the PBS devices are operable at alternative incidence angles other than 45°.

Figure 4:
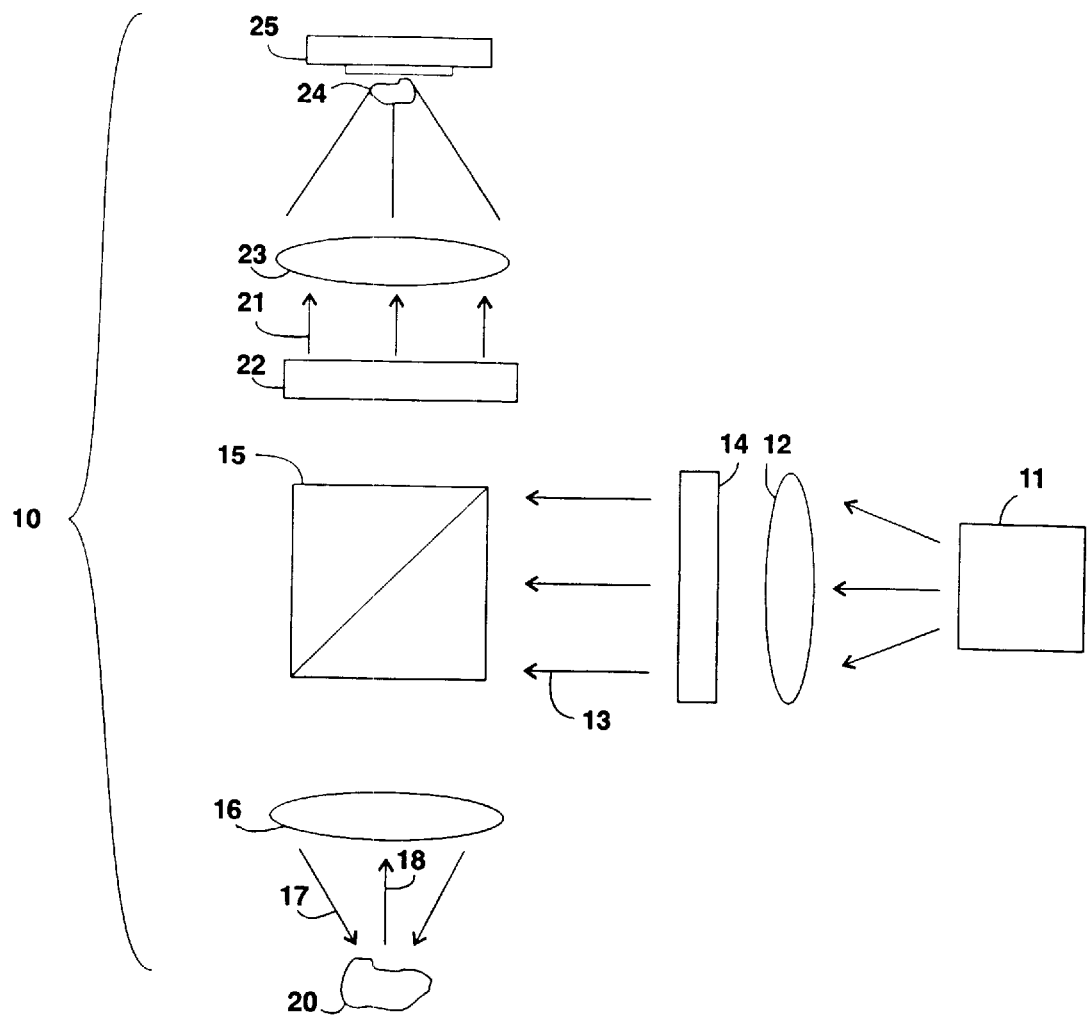
FIG. 4 depicts an imaging system constructed in accordance with the present invention.

FIG. 4 depicts a first embodiment of a system implementing the invention. An illumination source 11 provides optical radiation, and may be any suitable light source including by way of illustrative example a conventional light bulb, a laser, an arc lamp, a krypton lamp, a xenon lamp and a pulsed flash tube. The optical radiation from source 11 travels along an optical path in which associated optics 12 are located. The optical radiation passes through the optics 12 to a first spectral filter 14 that transmits light of a selected spectral range to a polarizing beamsplitter element 15, the functioning of which has been described in connection with FIG. 3. The selected light is thus reflected by PBS 15 and thereby directed to an objective 16, which further directs and focuses the light onto a sample 20 that is capable of responsively fluorescing and emitting light when so illuminated. A portion of the light emitted from the sample 20 is selectively passed by PBS 15 and is thereby delivered to imaging optics which include a second spectral filter 22 and image forming optics 23 that collect the fluorescent emissions from sample 20 to form an image 24 on a detector 25.

The present invention will find application in numerous fields such as imaging science, microscopy, optical design, birefringent filters, and tunable filters. The inventive system is especially suitable for use in many areas in which imaging is employed, such as drug assays, genetic or DNA analysis and fluorescent imaging.

Figure 5:
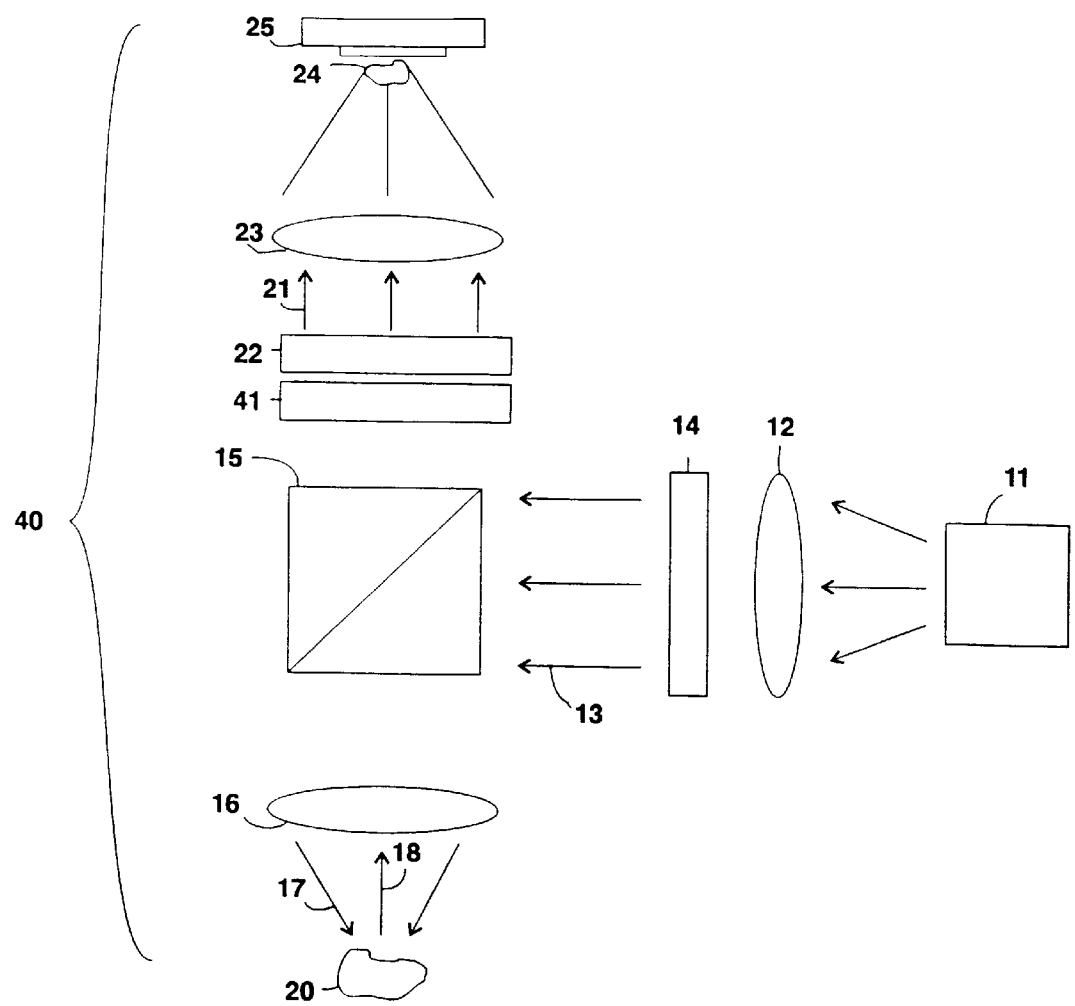
FIG. 5 illustrates another embodiment of an imaging system in accordance with the invention.

FIG. 5 depicts a modified form of the inventive system that additionally incorporates an optical filter 41 in the path of the imaging optics to provide additional rejection of any stray or scattered excitation light and thereby prevent such strong light from unintentionally contributing to the image developed at detector 25.

The wavelengths of optical radiation that are used for the excitation and emission bands may be selected for reflection and transmission within the system by the use, for example, of fixed filters, a filter wheel, or tunable filters such as acousto-optic tunable filters ("AOTF") or liquid crystal tunable filters ("LCTF"). A large number of independently chosen wavelength bands may be employed for excitation and for responsive emission with either type of tunable filter. Since the polarizing action of the PBS is effective over a wide spectral range, a similarly wide spectral range may be employed in the overall system. Moreover, inasmuch as the excitation and emission wavelengths may be independently selected, a system which collects emission light at a given wavelength when imaging one fluorescent species and then, after adjustment of the excitation and emission filters, uses this same wavelength for sample excitation can be constructed. It is not necessary to mechanically change the beamsplitter elements, even if the bands used at different times for excitation overlap with the bands used at different times for emission. For each selected excitation wavelength, a complete emission spectrum can be obtained over a broad range free of gaps or inaccessible spectral bands. The present invention is therefore advantageously suitable for use with spectral instruments to obtain spectra of fluorescent emission. Examples of such equipment include, without limitation, grating spectrometers, Michelson interferometers, Sagnac interferometers, and tunable filters such as AOTFs and LCTFs.

As noted above, the PBS may be operated at incidence angles $\theta_{inc}$ other than 45°. If operated in this manner, the angle through which the excitation light is reflected by the PBS will not be 90°, but another angle which is given by $2\theta_{inc}$. Also, while the optical system in FIG. 4 shows the excitation and emission beams perfectly oriented or coincidental with the optical axis of objective 16, it is possible to construct the system of the invention with excitation and emission beams oriented so their rays do not coincide with the optical axis of this objective. The off-set may be a small difference which arises as a consequence of manufacturing tolerances in constructing the system, or it may be an intentional difference of several degrees up to about 5°. Such a design may be utilized, if the objective has sufficient field-of-view, to reduce normal-incidence Fresnel reflections which would otherwise occur from the sample such as e.g. the glass surface of a microscope slide.

If a filter wheel is used to select the wavelength band of excitation light, the light source and filter wheel may be located separately from the remainder of the system and the excitation light may be introduced into the optics by means of a fiber optic bundle so that any mechanical vibrations of the wheel do not interfere with the remainder of the system or create image shifts.

As thus far described, the present invention images fluorescent emissions having a polarization orthogonal to the polarization state of the excitation light. This arrangement is suitable for imaging samples which emit substantially depolarized emissions. However, by incorporating a birefringent network between the PBS element and the sample, it is additionally possible to image fluorescent emissions having the same polarization as that of the excitation light. In this implementation, the birefringent network converts the polarization of the light in one wavelength band, such as the emission light, to the orthogonal polarization state without significant effect on the polarization of the other band, such as the excitation light. Use of the birefringent network thus permits imaging of either of the possible polarization states of the emission light and, as hereinafter described, preserves the desired rejection by the PBS element of stray excitation.

Figure 7:
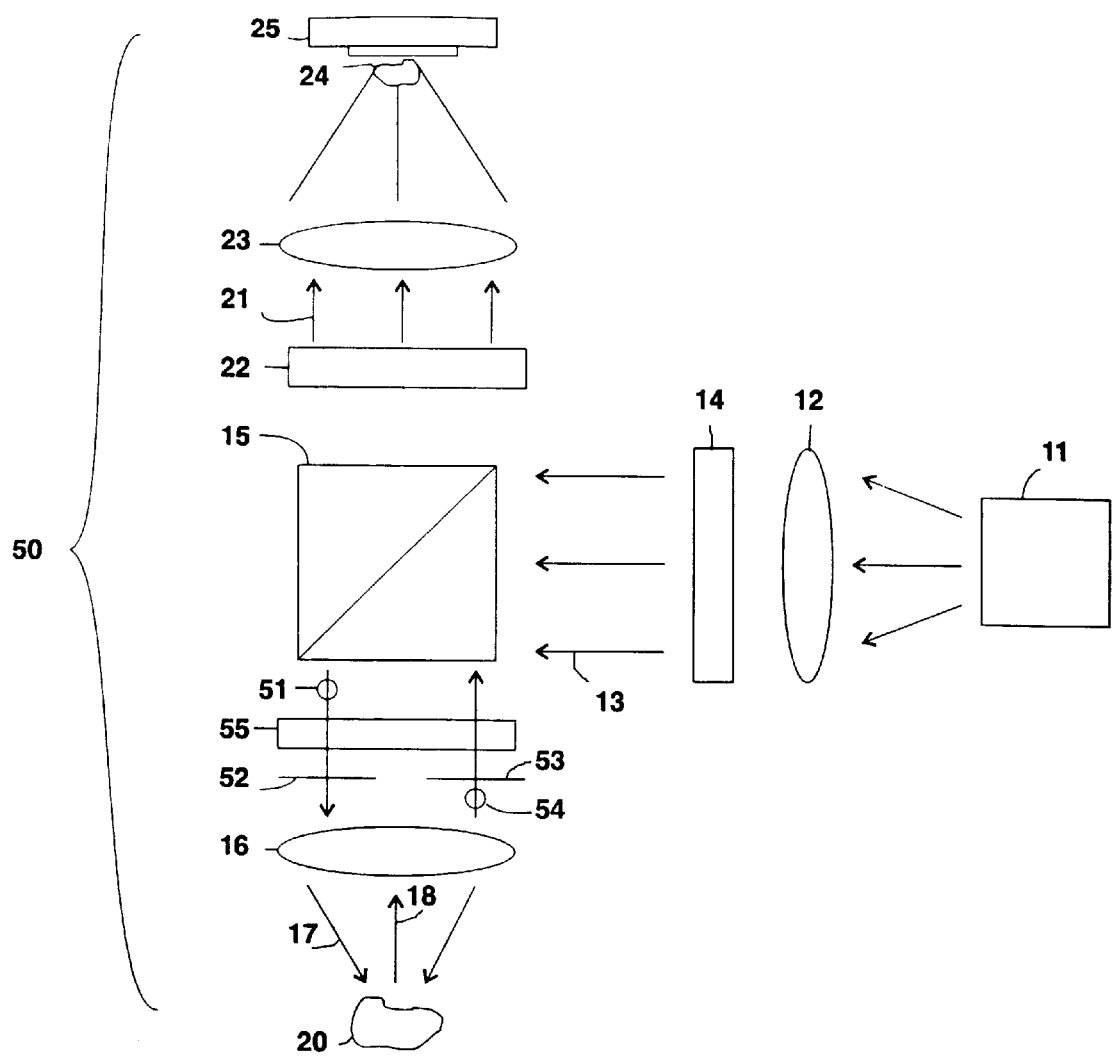
FIG. 7 shows another embodiment of an imaging system in accordance with the present invention.

Any birefringent network may be used in such an embodiment of the invention. The network may be as simple as a single optical retarder (birefringent element), or may comprise a complex arrangement including a plurality of retarders. When the network is a single retarder, it is positioned in the beam between the PBS element and the sample as shown in FIG. 7 (in which the birefringent network is identified by reference numeral 55). The retarder's fast axis is oriented at 45° to the polarization axis of the excitation light. Such an element has no effect on the polarization of light for those wavelengths at which the waveplate has integral order, i.e.

$R(\lambda)=m\lambda$ where $R(\lambda)$ is the retardance, $\lambda$ is the wavelength, and m is an integer. However, the same retarder will convert the polarization of light from one state to the orthogonal state at wavelengths for which it exhibits half-integral order, i.e.

$R(\lambda)=(m+\frac{1}{2})\lambda,$

The retarder may for example comprise a fixed retarder formed of polymers, quartz, calcite, or any other birefringent material. Alternatively, the retarder may be a liquid crystal cell having a fixed or a variable retardance. The retarder system may also be formed of both fixed and variable retarders placed in optical series. The choice of material will be determined by the particular system, as will be apparent to persons of ordinary skill; exemplary materials include nematic, smectic A*, and smectic C* materials, quartz, calcite, $LiNbO_3$, mylar, and optical retardation films sold commercially by Polaroid, Sanritz, Nitto Denko, and International Polarizer.

Figure 6:
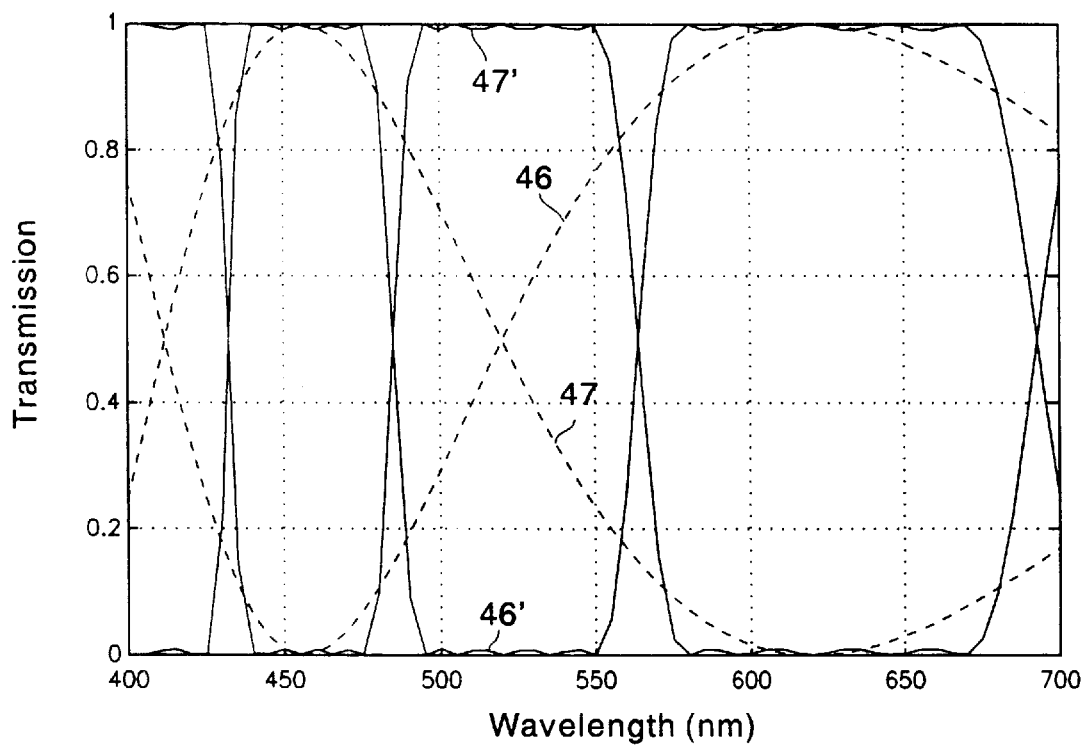
FIG. 6 graphically shows the properties of a birefringent network for light of various wavelengths.

FIG. 6 graphically illustrates the functioning of a retarder. Curve 46 shows the transmission of un-altered polarized light. For a single waveplate as referred to above, curve 46 exhibits maxima at wavelengths at which the waveplate has integral order, and minima at wavelengths for which it has half-integral order. Considering the complementary case, the curve 47 — depicting the efficiency of transforming light from a selected polarization state to the orthogonal state — exhibits maxima at wavelengths for which the waveplate has half-integral order, and minima at wavelengths for which the waveplate has integral order. A second set of curves 46' and 47' illustrate the corresponding properties of an exemplary birefringent network of three retarders.

FIG. 7 depicts a system of the invention incorporating a birefringent network 55 located optically between the PBS and sample; the retardance network 55 converts substantially all of the excitation light to its orthogonal polarization state with little effect on the light emitted by the sample. Excitation light from the PBS is polarized along an axis 51, and is converted by the network 55 to the orthogonal polarization state 52. The converted light 52 is directed to the objective 16 and then to the sample 20 from which it is reflected in the same state 52. As shown in FIG. 7, the reflected light is converted back to its original polarization state 51 by the network 55, and is rejected at the PBS 15. Emission light from the sample in state 53 or 54, on the other hand, proceeds through the network 55 without substantial alteration of its polarization state. From network 55, the emission light in state 54 is rejected at PBS 15 while emission light in state 53 is transmitted by and through the PBS to form the fluorescence image 24 on detector 25. This behavioral difference is a result of the different excitation and emission wavelengths. Thus, the retarder or retardance network 55 should be suitably selected to accommodate the particular wavelengths involved — i.e. so that the retarder or network efficiently converts light from one polarization state to the other at one wavelength band, but converts (at most) little of the light at the other wavelength band. The excitation light reflected from the PBS to the sample has the "S" polarization state 51 which is converted by network 55 to the "P" polarization state 52 and passed on to the sample. The sample is thus illuminated in the "P" mode. Reflected light from the sample has the "P" polarization state 52 which is converted back to the "S" state 51 as it traverses network 55 a second time; this S-mode light is reflected by the PBS and is thereby prevented from continuing on to the imaging optics. When the sample and/or fluorescent dye has even a partial orientation axis, it may be desirable to image the sample in the "S" and/or "P" mode with respect to the excitation and/or the emission light.

The emission light is not altered by the network 55. Since the PBS transmits only the "P" polarized light 53, the fluorescent image is formed by light which is emitted in the "P" polarized state; any "S" polarized light emitted by the sample is rejected at the PBS. Accordingly, the emission light imaged by the system has the same polarization state as that of the excitation light. With the use of a suitable birefringent network, the present invention is thus effective at rejecting the excitation light so that it does not interfere with the fluorescent image, even though the sample emission has the same polarization state as the excitation light.

In contrast, when no birefringent network is present, the excitation light has "S" polarization while the emission light has "P" polarization. Such a system images all randomly fluorescent emissions.

Figure 8:
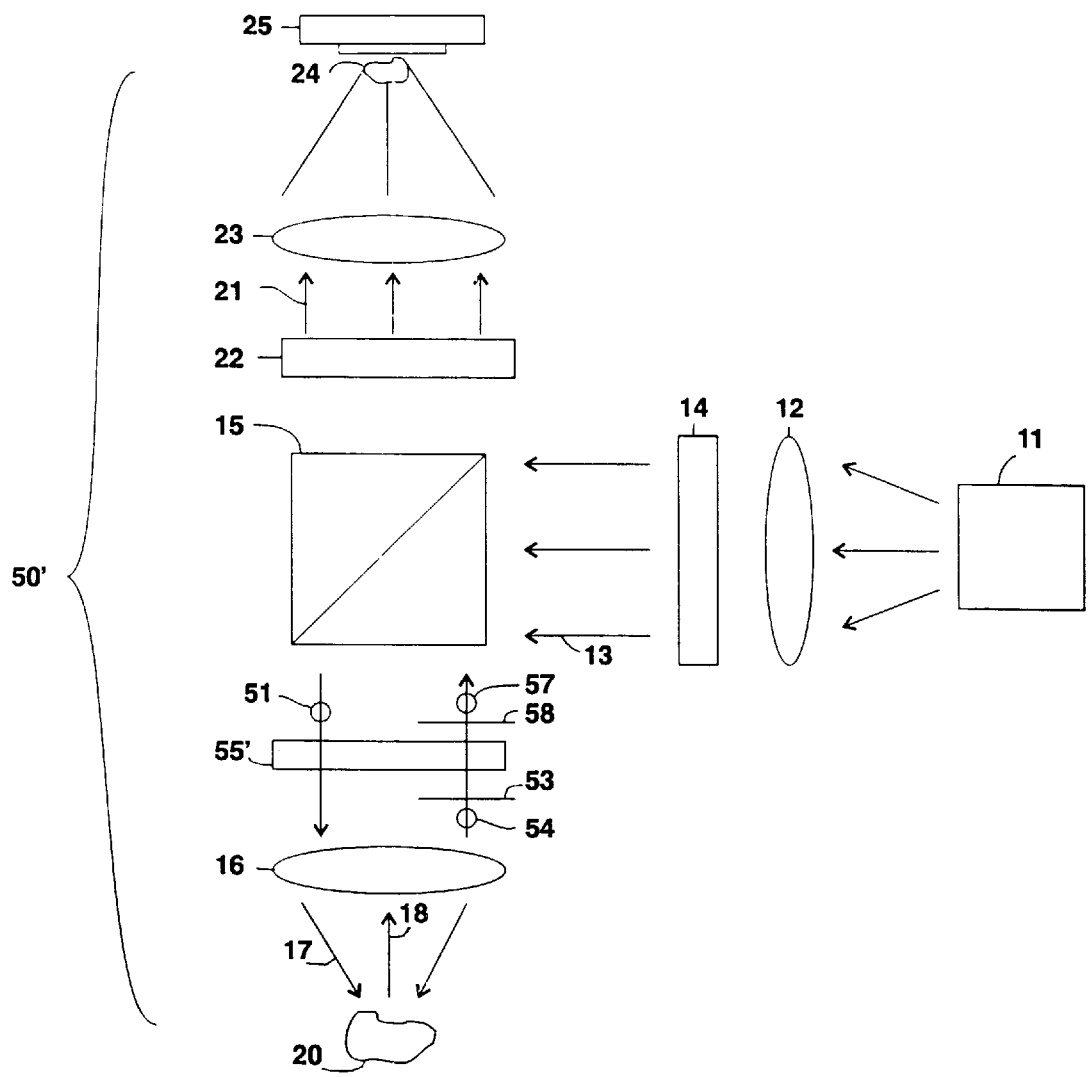
FIG. 8 illustrates still another imaging system in accordance with the invention.

The birefringent network works equally well if its action is reversed. That is, the birefringent network can alternatively transmit excitation light with an essentially unchanged polarization state and transform the polarization of the emission light from a selected state to the orthogonal state. This modification is illustrated in FIG. 8 where a birefringent network 55' is interposed between the PBS 15 and the sample 20. Excitation light from the PBS is "S" polarized, as indicated by reference numeral 51, and is thus unaltered by the network 55'. The excitation light proceeds to the sample, is reflected in the same state 51, passes again through the network without significant alteration, and is rejected at the PBS. Emission light in state 53 or 54 proceeds through the network 55' which converts light of polarization state 53 to state 57 and light of polarization state 54 to state 58. Converted emission light in polarization state 57 is then rejected by the PBS, while converted light in state 58 is transmitted by the PBS to form the fluorescence image 24 on detector 25.

The excitation light is "S" polarized when it illuminates the sample, and any reflected light is similarly "S" polarized. This light is essentially unchanged as it passes through network 55' so that it encounters PBS 15 as "S" polarized light and is reflected at the PBS. "P" polarized sample emission is converted by the network to the "S" state and is rejected at the PBS. Emissions from the sample in the "S" state are converted by network 55' to the "P" state and are transmitted through the PBS to form the fluorescent image 24. Once again, the system is effective at rejecting unwanted excitation light from the image, even though the sample emission and sample excitation have the same polarization state.

In the preceding example, all beams have an "S" state at the sample, while in the earlier example the beams are all "P" polarized. Some sample species have an intrinsic polarization sensitivity so that the polarization sense at the sample affects the overall fluorescence intensity; an example of such a sample is a fluorophore attached to a molecule which is bound to an oriented membrane. In these circumstances, the sample has a preferred polarization axis for optimum excitation and, for such samples, there is an important difference of result whether a system of the type shown in FIG. 7 (illumination with "P" mode light) or FIG. 8 (illumination with "S" mode light) is employed. Other systems in accordance with the present invention and which permit measurements along both the "S" and "P" polarization axes are described below.

Because polarization state conversion depends on the birefringent network to selectively convert the polarization state of either the excitation light or the emission light, but not both, the same birefringent network can be used for a variety of observations at a variety of wavelengths. If the excitation light is chosen to have a wavelength for which the network produces effectively no (or full) conversion of a selected polarization state to its orthogonal counterpart, and the emission light has a wavelength for which the network produces full (or no) polarization conversion, then the desired result will be obtained: the excitation light will be rejected at the PBS, while the imaging emission light that has the same polarization state at the sample that the excitation light had at the sample will be transmitted.

The birefringent network may comprise a single retarder in any system in which a narrow range of wavelengths is used for excitation, such as when the light source is a laser. However, such a network is unsatisfactory when a broader range of wavelengths is used since such a network only achieves the ideal polarization properties of complete conversion or completely unaltered transmission at the exact wavelengths for which the retarder exhibits, respectively, precisely half-integral or integral order. When light having a range of wavelengths is used, the network will produce a range of results, i.e. some unwanted transmission of unconverted light and some unwanted conversion, thus reducing the effectiveness of the system. Effective accommodation of a range of wavelengths requires a multi-element network.

One suitable class of multi-element networks may be constructed using the techniques described in a series of papers: "Optical Network Synthesis Using Birefringent Crystals. I. Synthesis of Lossless Networks of Equal-Length Crystals", J. Opt. Soc. Am. 54:1267 (1964) by S. E. Harris, E. O. Amman and I. C. Chang; "Synthesis of Optical Birefringent Networks", Progress in Optics IX (North-Holland, Amsterdam, 1971) pp. 123–177 by E. O. Amman; and "Flat Passband Birefringent Wavelength Domain Multiplexer", Electronics Letters 23(3), 106–7 (1987) by W. J. Carlsen and C. F. Buhrer. The entire contents of these papers is incorporated by reference. These papers describe synthesis of optical birefringent Solc filters that have a prescribed passband and stopband, based on a complex-exponential polynomial expansion similar to a Fourier series. While the technique of Harris et al. is quite general, it is sufficient here to consider a nominally lossless filter which accepts and emits light polarized at 0°. For this case, a filter transmission of 1 corresponds to no conversion of polarization state, while a transmission of zero corresponds to complete conversion from a polarization state with an axis of 0° to the orthogonal state with an axis of 90°.

For a mathematical description of the desired passband, the synthesis procedure yields a number of orientation angles. The filter is constructed by assembling a like number of retarders in optical series, with their crystal axes oriented at mathematically-specified orientation angles. Since the objective is to obtain a wavelength-dependent polarization conversion rather than a wavelength-dependent modulation of optical intensity, the entrance and exit polarizers, which are normally used in a birefringent filter to convert polarization state changes into intensity changes, are omitted. Only the birefringent network is required.

Carlsen and Buhrer describe the use of this technique to construct filters with entrance and exit polarizations of 0°, with equal-width passband and stopband, and exhibiting nearly a flat response within each band with a periodic ripple of 1% or less. This ripple magnitude is a design parameter analogous to the ripple parameter used in the design of equiripple (Chebyshev) filters well-known to electronics engineers. A filter constructed in accordance with the Carlsen and Buhrer method with the intensity converters omitted, is suitable for use in systems implementing the present invention. The network should be oriented so that the 0° axis (the nominal entrance polarizer axis) of the filter is parallel to either the "S" or "P" state.

The result is a network with a set of maximally wide spectral bands over which there is very little polarization conversion, and a complementary set of bands over which there is substantially complete polarization conversion. This provides a first set of wide spectral regions over which to excite the sample, and a second set of wide regions over which to collect the emitted light. Ideally, the network should be designed so that each type of light, excitation and emission, fits entirely within either a passband (no conversion) or stopband (full conversion) of the network, with little or no spill-over.

Figure 9:
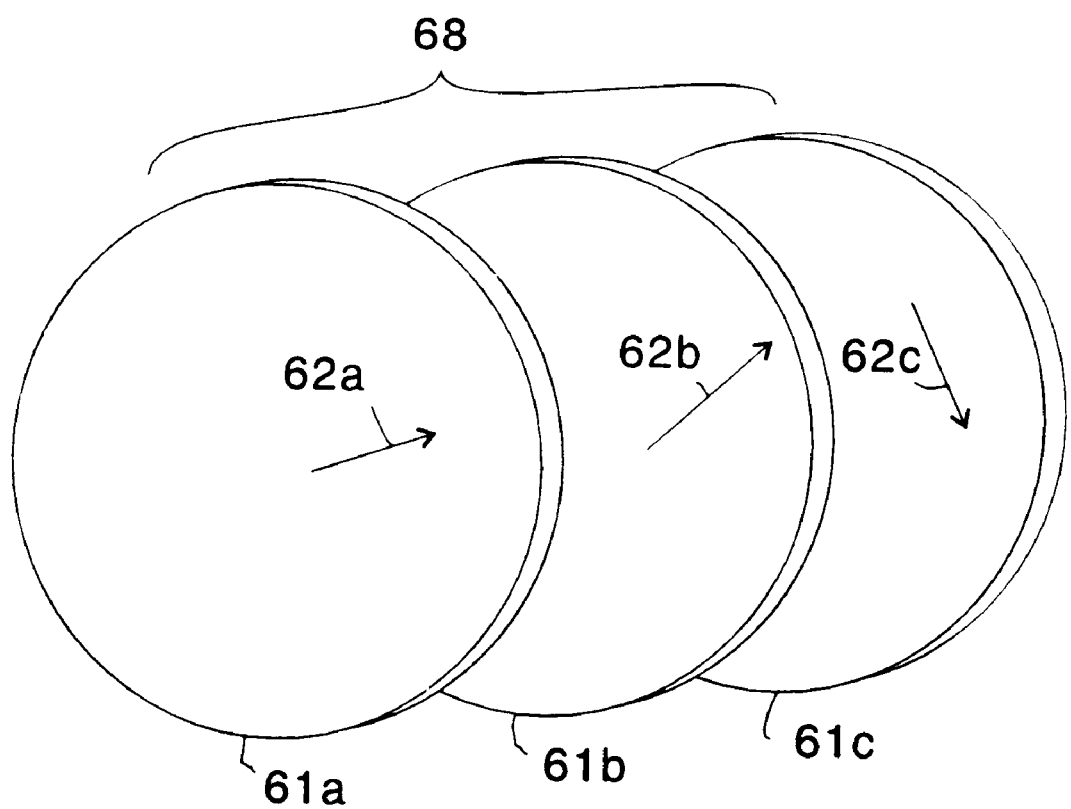
FIG. 9 shows a construction of a non-switchable birefringent network.

Such a network may for example be constructed in the manner shown in FIG. 9, where the elements 61a and 61b are constructed so that each has exactly twice the optical retardance of element 61c, and the fast axes 62a–62c are oriented at angles of 80.1°, 104.5° and 45°, respectively. When retarder 61c is chosen to have exactly one-half the retardance of elements 61a and 61b, the network yields a flat-topped response and the maximally wide passband and stopband described above. The spectral location of the passbands and stopbands are a function of the retardance values of the elements 61a–c, as is well-known in the art. By way of non-limiting example, quartz elements with thicknesses of 0.007" for 61c and 0.014" for 61a and 61b may be used.

To selectively change the passbands and stop bands, a replaceable birefringent network may be mechanically introduced and removed from the beam between the PBS and the sample. It is preferable to replace the network with another optical element having a comparable thickness and optical refractive index to avoid focus variations and image shifts when the network is switched in and out of the optical path. The replacement element may be a second birefringent network, a planar optical window, or any other optical element.

Figure 10:
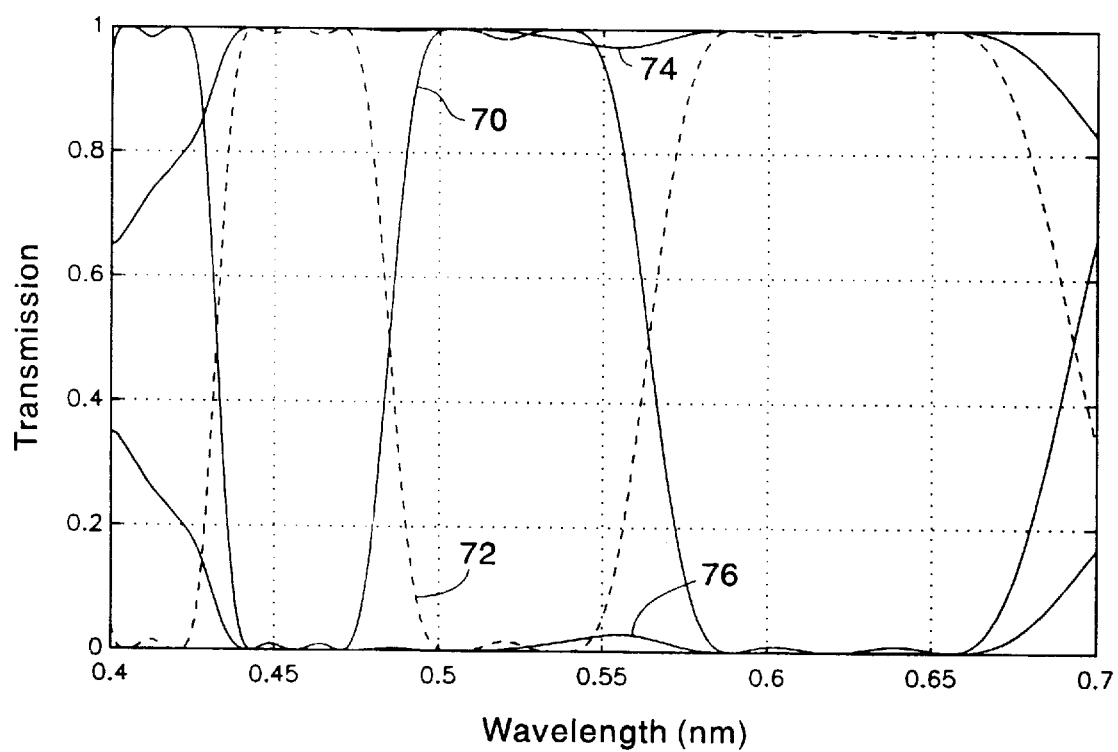
FIG. 10 graphically illustrates the properties of a switchable birefringent network for light of various wavelengths.

FIG. 10 graphically illustrates the properties of a switchable birefringent network for light of various wavelengths. At a first setting of the switchable network, the network transmits light of a specified polarization state, or converts it to the orthogonal polarization state, depending on its wavelength. Spectral curves 70 and 72 illustrate (for this first switch state) the efficiency of light transmission for a specified linear polarization of an unaltered state and the efficiency of conversion into the orthogonal state, respectively. For the other setting of the switchable network, the network transmits polarized light of all wavelengths without significant conversion into the orthogonal polarization state. Spectral curves 74 and 76 depict for this other switch setting the efficiency of light transmission for a specified linear polarization in the unaltered state and the efficiency of conversion into the orthogonal state, respectively.

In a preferred embodiment, the system includes an optical polarization switch such as a liquid crystal cell which acts in association with the birefringent elements. The switch has at least one setting at which the overall optical effect of the birefringent network is to transmit light within a specified range of wavelengths without alteration of its polarization state.

Preferably, the switch has a second setting in which at the overall optical effect is to convert light within a first selected wavelength range from a selected polarization state to the orthogonal polarization state, and to transmit light within a second selected wavelength range without significant change to its polarization state.

Figure 11A:
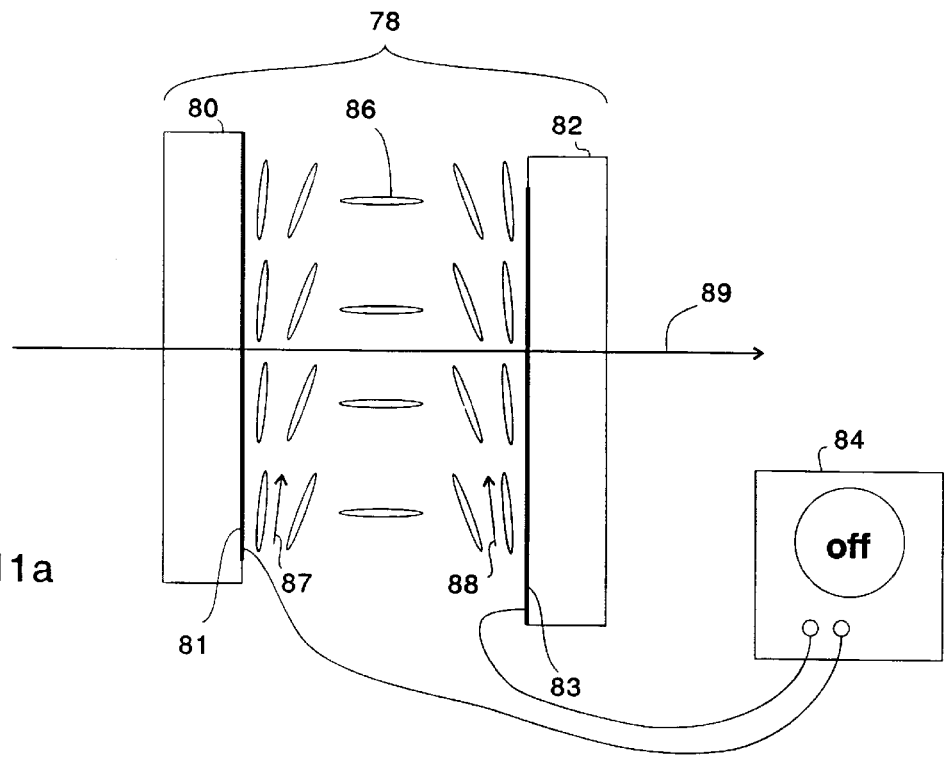
FIGS. 11a and 11b depict a suitable switch, in its respective "off" and "on" states, for use in constructing a switchable birefringent network.
Figure 11B:
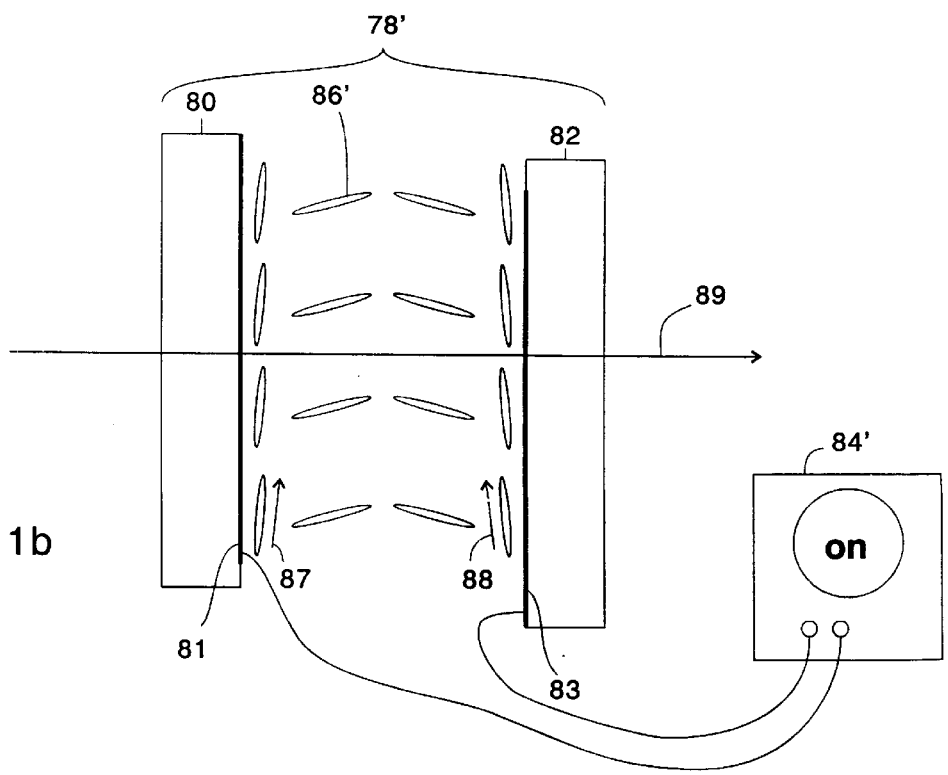

FIGS. 11a and 11b depict by way of example a suitable switch for use in constructing a switchable birefringent network, in the form of a variable optical retardance type liquid crystal cell which exhibits approximately $\lambda/2$ retardance for light of a specified wavelength range. It should be noted that FIGS. 11a and 11b are not to scale, and for purposes of clarity, show certain very thin layers as enlarged. The cell 78 is shown in the voltage-off state in FIG. 11*a,* and is shown and identified as 78' in the voltage-on state in FIG. 11*b.* The cell comprises two substrates 80 and 82 with transparent electrodes 81 and 83 on the respective inner surfaces 87 and 88 thereof connected to a voltage source 84. The layer or volume between the substrates 80 and 82 is filled with a nematic liquid crystal material 86, oriented by pretreatment of the inner surfaces of the substrates to have a preferred molecular alignment direction at the two surfaces 87 and 88. Light passing through the cell has an optical axis 89.

Figure 12:
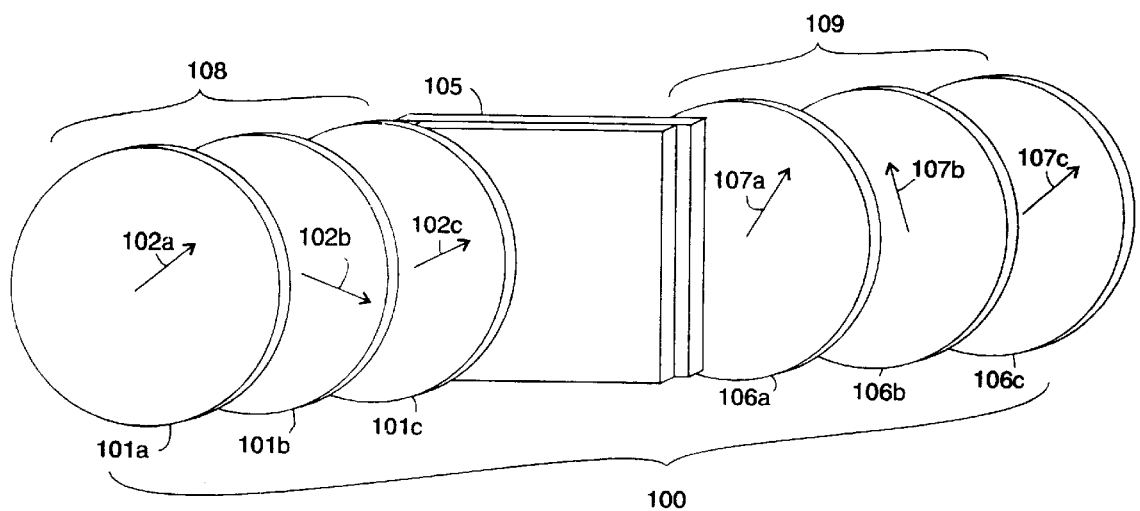
FIG. 12 illustrates a construction of a switchable birefringent network.

Referring now to FIG. 12, a switchable birefringent network 100 comprising a first retarder network 108 of retarder elements 101*a,* 101*b* and 101*c* and having fast axes oriented at respective angles 102*a,* 102*b,* and 102*c* is shown with a liquid crystal switch 105 and a further retardance network 109 comprising retarder elements 106*a,* 106*b,* and 106*c* having respective fast axes at angles 107*a,* 107*b,* and 107*c.*

Switchable versions of birefringent networks are disclosed in Miller and Buhrer's concurrently-filed co-pending patent application entitled "Tunable Optical Filter with White State", the entire contents of which are expressly incorporated by reference herein. As described earlier herein, these networks may be incorporated into the present invention to provide additional versatility to the system. In one switch state, the network is effectively absent from the optical path, whereas in the other switch state the network functions in the manner of the above-described non-switchable birefringent networks. The use of a switchable network enables independent measurements of the sample emissions to be readily obtained in either polarization state, so that fluorescence polarization anisotropy and other measures of interest may be assessed without need for any moving parts.

Figure 13:
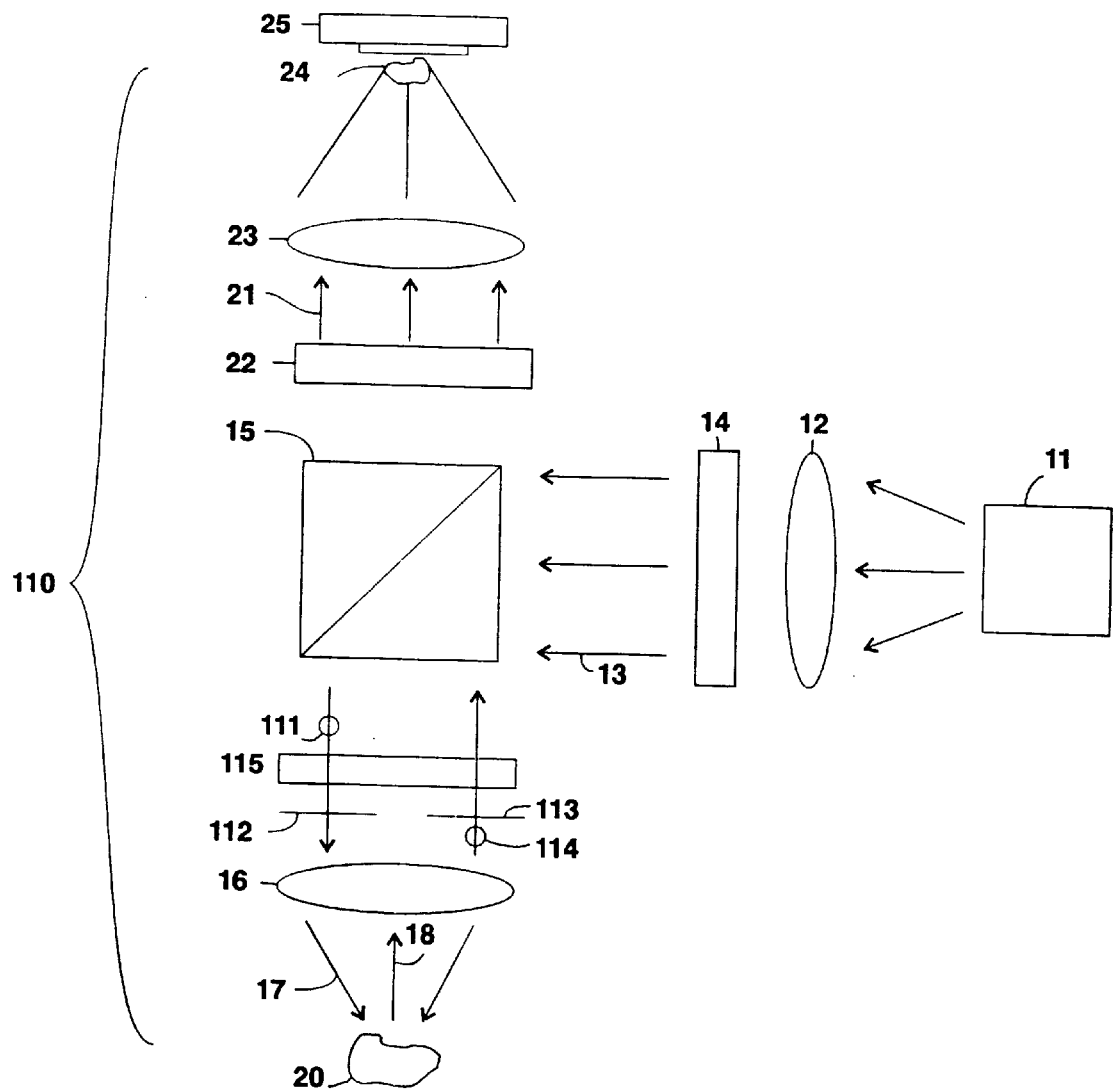
FIG. 13 depicts yet another embodiment of a fluorescent imaging system of the invention incorporating a switchable birefringent network.

A fluorescent imaging system 110 constructed in accordance with the invention and which incorporates a switchable birefringent network 115 interposed in the optical path between the PBS 15 and the sample 20 is shown in FIG. 13. In that embodiment, excitation light from PBS 15 is polarized along an axis 111. When the switch is in one setting, the polarized light is converted by network 115 to the orthogonal polarization state 112 and then proceeds through the objective 16 to sample 20. At the sample, the light is reflected in the same state 112, is converted back to state 111 by the network, and is rejected at the PBS. Emission light in state 113 or 114, on the other hand, proceeds through the network 115 without substantial alteration to its polarization state. Emission light in state 114 is rejected at the PBS while light in state 113 is transmitted therethrough and forms the fluorescence image 24. When the switch of the network 115 is in its other setting, the network has substantially no effect on the polarization of either excitation or emission light. As a consequence, unaltered "S" polarized excitation light from the PBS proceeds through the switchable network and illuminates the sample, from which any reflections are "S" polarized and proceed, without alteration, back through the network and are rejected at the PBS. Fluorescent emissions from the sample pass without alteration through the network 115; "S" polarized emissions are then rejected at the PBS while "P" polarized emissions proceed through the PBS to the imaging optics and form the fluorescent image 24. In summary, an image obtained in the first switch state reveals the fluorescence emissions having the same polarization state as the excitation. In the other switch state, the image reveals the emissions polarized orthogonally to the excitation light.

A suitable switchable birefringent network can be constructed using, by way of example, 6 quartz elements oriented with their fast axes at respective angles of −44, +22, −23.3, +113.3, +68 and +134 degrees. Elements 2 and 5 have exactly twice the retardance of the other elements. Positioned between the third and fourth quartz elements is a liquid crystal variable retarder with an optical axis oriented at 0° and a retardance that is switchable between approximately $\lambda/2$ and approximately 0 for light in the wavelength range of interest. This may for example be achieved with a nematic "pi" cell having substrates of Corning 7059 glass coated with ITO on the inner surfaces to achieve a conductivity of 200 ohms/square, and spaced apart at a separation of 4 microns. The region disposed between the substrates is filled with nematic mixture ZLI-2772 (EM Industries, Hawthorne, N.Y.), which is free of any chiral twist agents. The inner surfaces of the substrates are buffed, in accordance with established methods in the art, to produce a parallel (splay) orientation at 0° with a pre-tilt angle in the range of at least about 2°.

When a square-wave voltage of 25 Volts at 2 kHz is applied to the cell, the overall network converts the polarization state of certain wavelengths of light but not others, with approximately equal portions of each, and a ripple of approximately 1% in the passband (no conversion) and stopband (complete conversion) (FIG. 11*b*). When the voltage is removed, the liquid crystal molecules re-orient in 1–2 milliseconds so that the overall network no longer converts the polarization state of either excitation or emission light. This state persists for approximately 40 ms, after which time the liquid crystal cell undergoes a transition to a metastable state shown in FIG. 11*a.* The unwanted effects of this transition may be avoided by applying a "tickle" voltage or periodic "refresh" signal to the cell, as is well-known in the art.

A twisted-nematic liquid crystal cell may also be interposed between the PBS and the sample. Such a liquid crystal element rotates the polarization state of light by the twist angle, which is usually about 90°, and thereby affords a way to selectively illuminate the sample with either "S" or "P" polarized light. Engaging or energizing the cell also selects whether "S" or "P" polarized emission light is measured at the detector. The liquid crystal cell may be used in combination with the above-described birefringent networks to select whether the emission light being measured has the same polarization state as, or the state orthogonal to, that of the excitation light.

In constructing a system which employs a twisted-nematic liquid crystal cell, it is important that the cell produce the desired rotation at both the excitation and emission wavelengths. While there is generally some degree of variation with wavelength, the variation may be minimized. One way to do so is to use a cell for which the product of thickness and birefringence is large compared to the wavelength of light, i.e. the product is at least $3\lambda$. This first approach relies on the principle of adiabatic following and is highly successful over a broad spectral range. A cell with a 15 micron layer of the liquid crystal material ZLI-2772, having a 90° helical twist, is for example suitable for use in the visible range. Another approach is to use a cell that is operated near the first or second Gooch-Tarry minimum for the specified wavelength range. Such a cell is commonly well-known in the art and is termed a "first-minimum" or "second-minimum" cell; sources of these cells include Excel Technology (Belle Meade, N.J.) and Standish Industries (Lake Mills, Wis.).

In the foregoing, several birefringent systems have been described which vary the polarization state of the excitation light and/or the emission light, without defeating the barrier provided by the PBS against excitation light contributing to the fluorescent image. It is possible to use several birefringent networks, or one or more birefringent networks in series with a twisted nematic liquid crystal cell, to combine the functions. This enables varying the polarization state of the excitation light, the emission light, or both. Also, several switchable birefringent networks may be employed to provide operation at a variety of wavelengths.

Sequential mechanical engagement and disengagement of components, or sequential application and removal of electrical signals to the liquid crystal elements, may be used to produce sequential illumination of the sample in each of the two orthogonal polarization states and/or viewing of the sample in each of the two orthogonal polarization states. This is useful in measurements of fluorescence polarization.

Systems constructed in accordance with the present invention are free of the NA restrictions inherent in the dark-field approach. Thus, such systems are capable of high throughput in this regard, i.e. use with high NA objectives such as the element 16 in FIG. 4.

Since polarized light is required for illumination but many light sources do not inherently generate a polarized beam, the available energy density at the sample using an unpolarized source is likely to be no greater than about half that of an equivalent unpolarized system. Accordingly, unless a polarized light source is available, as may be provided with lasers, a prolonged and perhaps doubled exposure period may be required to produce an equal amount of fluorescent emission energy to unpolarized prior art systems.

On the other hand, "photobleaching" of the sample is also reduced in the inventive systems by about one-half, so that longer exposure periods generally will not cause a problem, except for the slower image acquisition rate of the instrument. Furthermore, many current instruments incorporate neutral-density filters to reduce the excitation flux and reduce photobleaching. In these cases it is therefore a straightforward procedure to reduce the amount of otherwise-utilized neutral-density filtration to yield the same excitation flux at the sample as prior art arrangements when using a system of the present invention.

When it is critical that total excitation flux be maximized, special techniques which preferentially convert the polarization state of lamp-based sources so that the majority of the lamp flux is in the desired polarization state may be employed. By way of non-limiting example, a reflective polarizing film comprising a thin polymeric substrate (in contrast to a coating on a glass surface), together with a $\lambda/4$ waveplate to maximize total excitation flux by means of converting one polarization state to the other may be used. The film may be encapsulated in a glass or plastic such as a polycarbonate. DBEF film from 3M Corporation, for example, is a polarizer which transmits light of the desired polarization state and reflects the unwanted state. The film is placed after the $\lambda/4$ plate whose fast axis is oriented at 45° to the DBEF polarization axis. Approximately 50% of the incident light from an unpolarized source will be transmitted in its first interaction with these elements. However, the remainder of the incident light will not be transmitted but will, instead, be reflected back towards the illumination optics through the $\lambda/4$ waveplate. Some fraction of that light is reflected again by the illumination optics back toward the film, passing a second time through the $\lambda/4$ waveplate before again encountering the DBEF film. Since two passes through a $\lambda/4$ waveplate will convert linearly polarized light to its complementary state, any light rejected in the first attempt will then be properly polarized to pass through the DBEF film.

To obtain best performance, the illumination system should preferably be designed to control depolarized scatter and reflections. Such a system design must insure that light reflected by the DBEF film back into the illumination optics is not obstructed by opaque elements such as the lamp arc or filament, or by lamp supports and the like. The system is preferably designed to permit multiple passages of the light without excessive losses to beam divergence and vignetting. Properly implemented, arrangements such as this can increase the excitation efficiency to well above 50%. Furthermore, since the DBEF film acts as an entrance polarizer to the PBS, it notably improves the degree of polarization extinction in that component.

Another concern is that since only half the fluorescent emission is utilized (for a depolarized emission), at first glance the present invention appears to utilize only half of the emission light of a conventional epi-illumination system. However, many current imaging systems employ filters or other elements which are polarization sensitive and thus already sustain a similar loss. In other instances, the loss in prior art systems is not inherent in the measurement but arises from the use of an imaging technology that is itself based on polarized light. A non-limiting list of such polarization-sensitive elements includes diffraction gratings, liquid crystal tunable filters (LCTFs), acousto-optic tunable filters (AOTF's), surface plasmon filters, and cameras which incorporate any of these elements.

More importantly, systems which utilize epi-illumination beamsplitters with multiple excitation and emission bands are rarely efficient in their use of emission light because of the above-mentioned limitations of the dichroic beamsplitters. Often, the emission band is not sufficiently broad, or is not appropriately located to capture all of the fluorescent energy. Such filtration losses rival, or exceed, the polarization losses in systems of the present invention. Thus, in comparing losses in multi-band systems, the epi-illumination approach is efficient in terms of polarization but spectrally lossy (inefficient) because the filtration of the beamsplitter is not spectrally well-matched to the emission energy. On the other hand, the present invention exhibits excellent spectral matching between the filters and the emission energy. Which approach has higher throughput for a particular application depends on which fluorescent species are being imaged, how their spectra compare with the response of the dichroic beamsplitter, and whether other elements necessary to the system impose a polarization-selectivity of their own.

The present invention is ideally suited for use with polarization-dependent elements such as LCTFs, AOTFs, and surface plasmon filters. As compared with existing dichroic epi-illuminated systems, systems of the present invention exhibit no loss in efficiency and afford complete spectral freedom to excite and to collect images at any desired wavelengths. These features make the present invention ideal for multi-spectral imaging and imaging spectroscopy.

In some cases, it may be desired to illuminate the sample through a mechanical filter wheel. However, having eliminated mechanical motion in the remainder of the system, it is not desirable to introduce vibrations through the filter wheel. Thus, it is often beneficial to locate such a filter wheel separately from the remainder of the system and to couple the excitation light into the PBS by means of fiber and associated optics.

Figure 14:
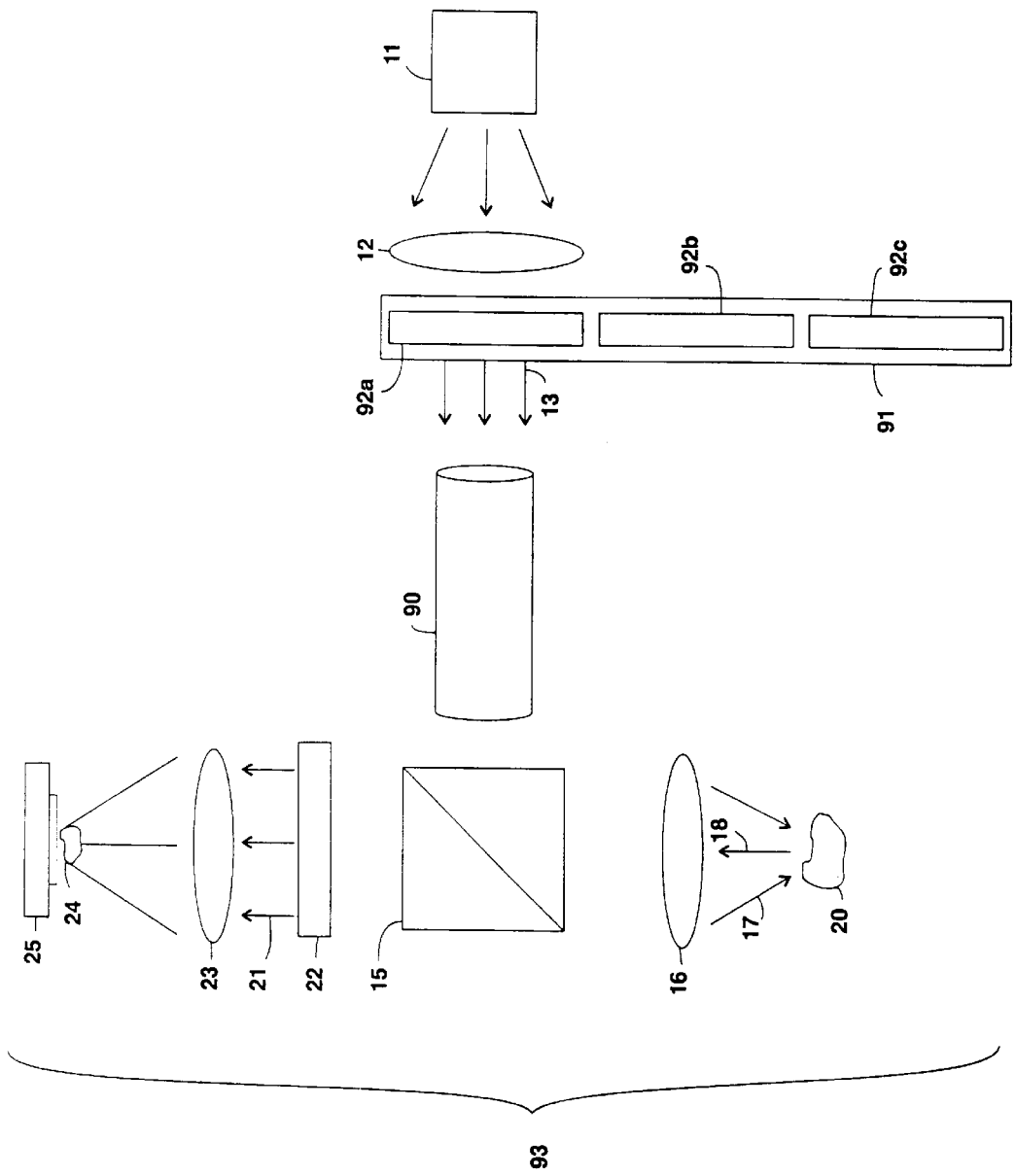
FIG. 14 shows still another embodiment in accordance with the invention in which the illumination system incorporates a fiber-optic feed.

FIG. 14 depicts such an embodiment of the invention in which the illumination system includes a fiber-optic feed 90. As there shown, a filter wheel 91 holding filters 92a, 92b, and 92c is used to select the excitation wavelength. Wheel 91 is located separate from the remainder of the system so as to eliminate vibration and image distortions as the excitation wavelength is changed. While a fiber optic system can thus be used to direct the excitation light (inasmuch as there is no need to preserve a spatially coherent image of the light source when illuminating the sample), a fiber optic system may not be employed in the emission path since this would degrade, or destroy, the spatial information forming or comprising the image of the sample. By providing a high-quality optical path for the emission light free of mechanical motion and vibration, the present invention is distinct in purpose from prior art arrangements and cannot utilize a fiber optic system on the emission or imaging side.

The imaging optics direct the emission light to a detector which views the fluorescent image. It is possible to use nearly any detector 25 with suitable signal-to-noise and detection performance. A non-limiting list of suitable detectors includes the human eye; photographic film; a CCD camera (such as the Model Micromax KAF-1400 from Princeton Instruments); a vidicon tube; an image intensifier tube or microchannel plate; and an avalanche photodiode, photomultiplier tube, or photodiode when only a single spatial reading is required.

Figure 15:
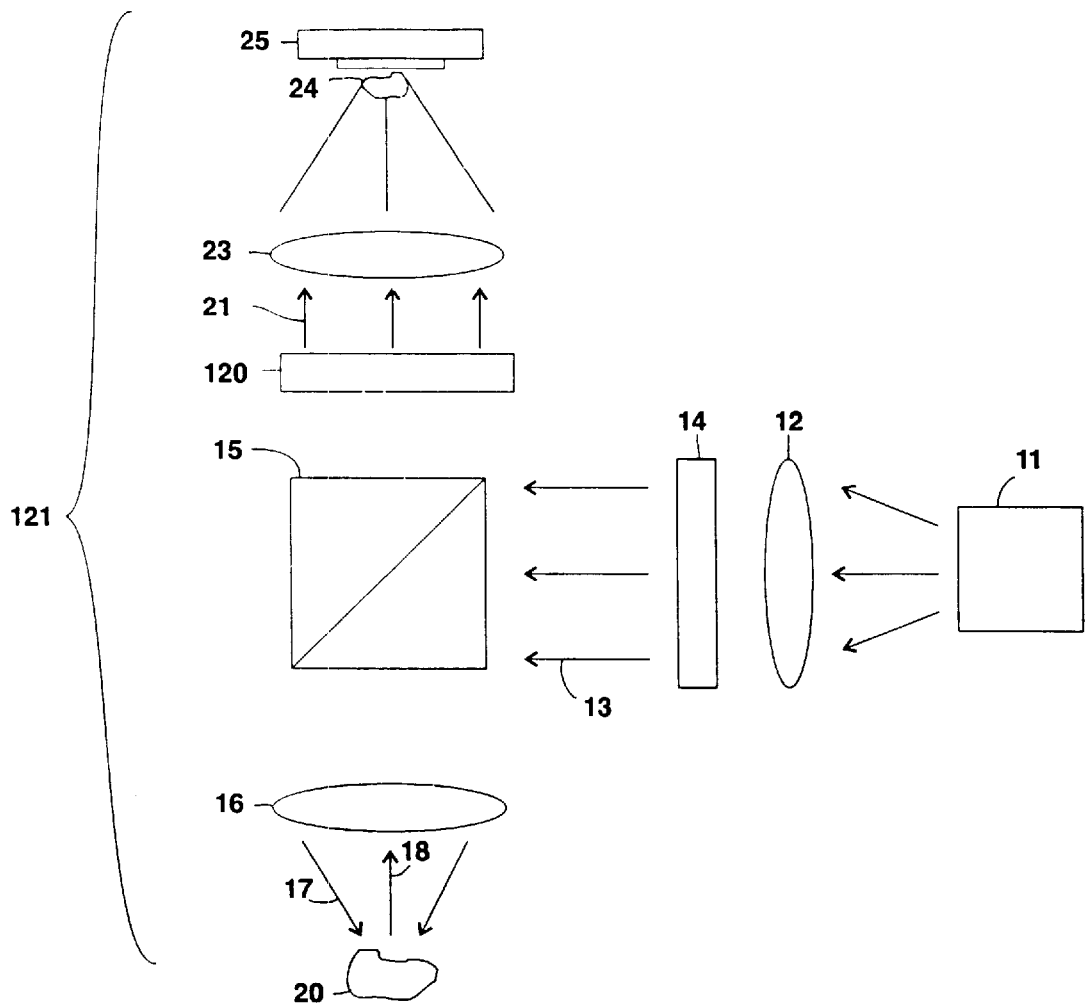
FIG. 15 depicts another embodiment of the present invention in which the imaging system incorporates a tunable filter or spectrometer in the emission path.
Figure 16:
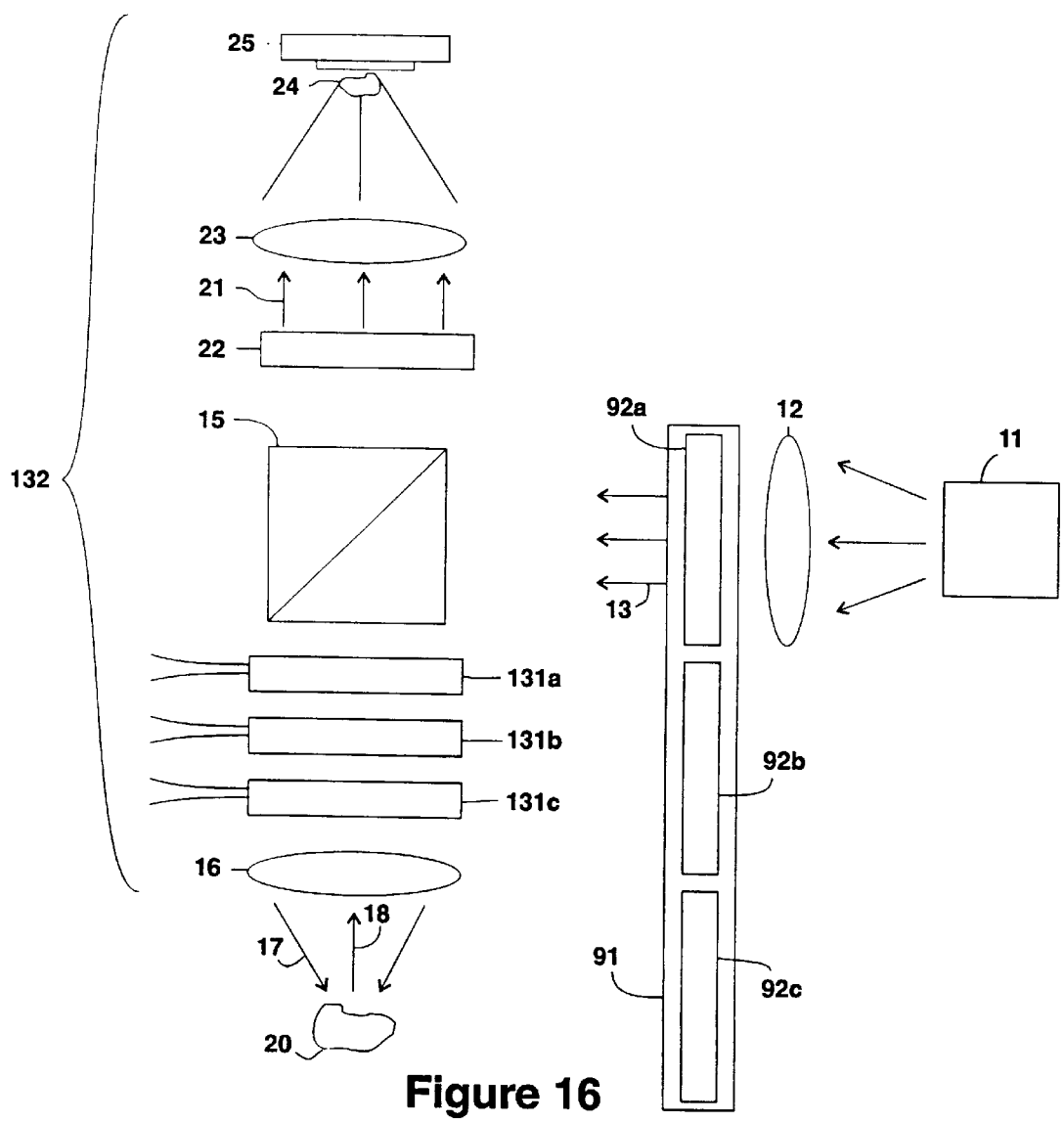
FIG. 16 shows an imaging system in accordance with the invention in which the system incorporates a filter wheel or tunable filter in the illumination path.

FIG. 15 shows a system in accordance with the present invention having a tunable filter or spectrometer 120 disposed in the emission path. FIG. 16 shows still another system of the invention including a filter wheel or tunable filter in the illumination path and a plurality of birefringent networks 131a, 131b, and 131c between the PBS 15 and sample 20.

Although it is within the intended scope of the invention to construct an imaging system using individual components and elements, it is more economical to construct or implement the system using an existing fluorescence microscope, such for example as the Axiovert 135 or Axioskop made by Zeiss (Jena, Germany), or the BX 60 from Olympus, or the E 800 from Nikon. These existing microscopes conveniently provide suitable illumination and imaging optics with high efficiency and good optical quality.

Conventional fluorescence microscopes include a structure for incorporating a dichroic reflector that is typically mounted on a slider or other removable member. The dichroic reflector may be replaced in accordance with the invention with a PBS that is dimensionally compatible with the available space.

The PBS may be a cube design, a plate design, or a double-refraction device such as a Rochon or Glan-Taylor prism. Another alternative is to use a DBEF film as the PBS. DBEF is typically provided in sheet form, and may be laminated between high-quality glass flats of e.g. BK-7 from Schott (Duryea, Pa.) by means of optical cement or epoxy such as UV-15 from MasterBond (Hackensack, N.J.). The exterior glass faces should be anti-reflection coated so that Fresnel reflections do not interfere with, or destroy, the otherwise high degree of polarization efficiency.

The degree of selectivity provided by the PBS alone may not be as high as desired. However, the selectivity of the instrument can be improved by a system of the invention constructed as shown in FIG. 17.

Figure 17:
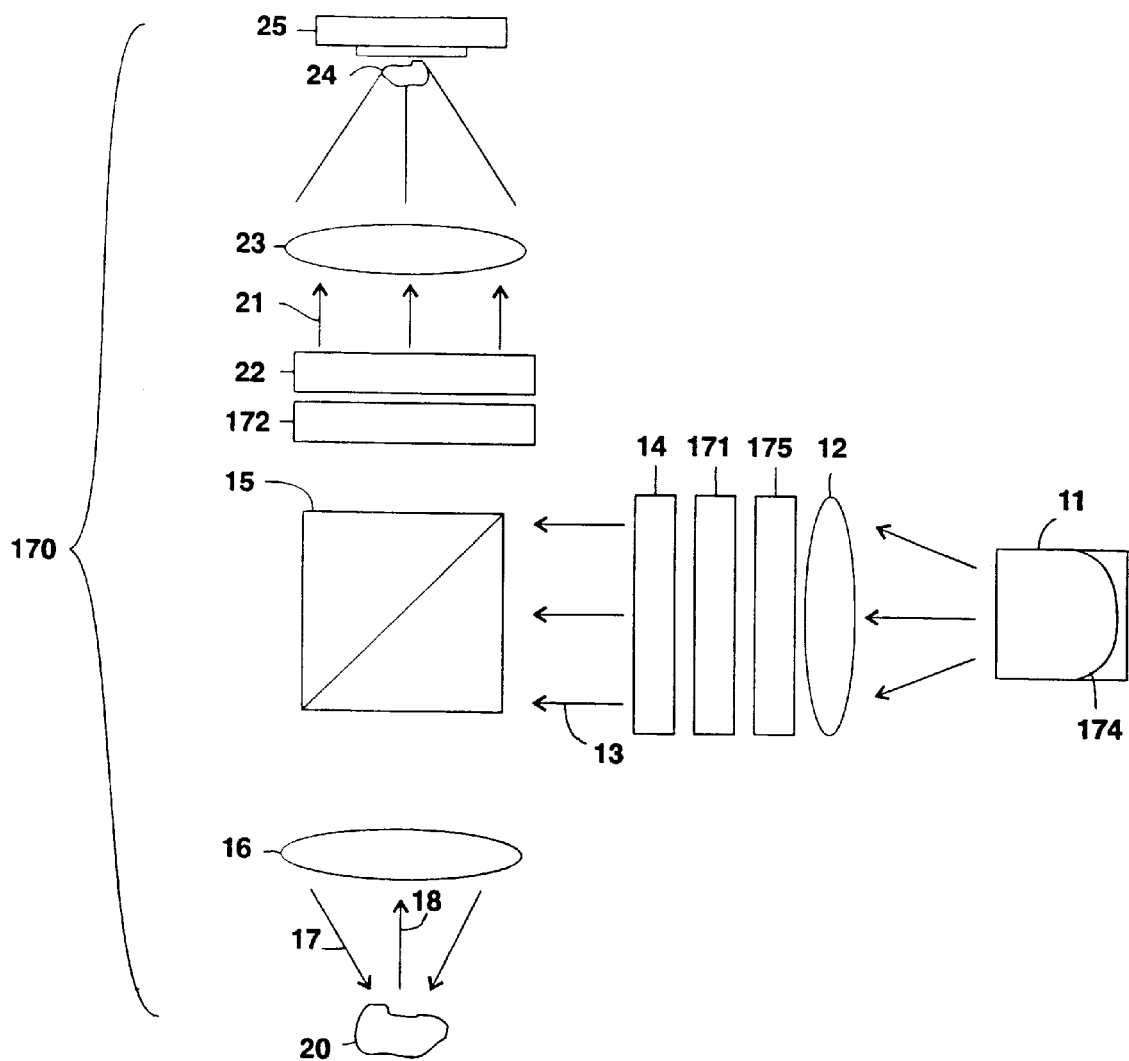
FIG. 17 shows still another imaging system of the invention in which the system incorporates one or more reflective polarizer elements located between the polarizing beamsplitter and other components of the system.

FIG. 17 depicts an imaging system 170 that further incorporates a polarizing element 171 which at least partially polarizes the excitation light 13 incident upon the PBS 15. The polarizing element 171 may optionally comprise a reflective polarizer element or, in another embodiment, a reflective polarizer element incorporating a $\lambda/4$ wave plate 175. Polarizing element 172 in the emission path at least further polarizes the partially polarized emission light that exits the PBS and is incident upon the element 172. These elements further perfect the polarizing action of the PBS.

In yet another embodiment a reflector 174 is located to direct light reflected by the reflective polarizing element back towards the reflective polarizing element. Reflector 174 can be behind the light source or incorporated as part of the light source housing.

In the embodiment illustrated in FIG. 17, the first location for a polarizer, identified as 171, is at the entrance face at which the excitation light is introduced to the PBS 15. First polarizing element 171 ensures that only "S" mode linearly polarized light is presented to the PBS and that any imperfections at the first interaction between the excitation light and the PBS will introduce only a loss in efficiency rather than a reduced polarization purity. The second location for a polarizing element, identified as 172, is at the exit face of the PBS 15 for admitting light from the PBS to the imaging optics 23. A linear polarizer 172 so placed removes stray "S" polarized light from the emission beam and increases the polarization purity of the PBS for transmitted "P" light. Performance limitations whereby some "P" light is reflected at the PBS hypotenuse do reduce the efficiency of collection for emission light, but this is generally an acceptably small amount on the order of 1% or less; this emission light is reflected into the illumination optics, where it should not normally cause a problem.

In implementing systems in accordance with the invention, any polarizer which operates in the required spectral range may be used. A nonlimiting list of such components includes commercial sheet dichroic polarizers such as: HN32, HN-38S or HN42 from Polaroid (Norwood, Mass.) and similar products for the visible range; HNP'B for the UV range and HR for the near-infrared, both from Polaroid; calcite prism polarizers such as the model RA-10-10 Rochon polarizer from Karl Lambrecht (Chicago, Ill.); and DBEF material from 3M Corporation. The latter class of materials is best operated either at normal incidence or at an off-normal angle, with the optimum choice depending on the overall system design.

The near UV ranges may be important for the excitation of particular fluorescent dye species. The excitation range may be extended by taking advantage of the fact that the PBS need only afford reflection, not true polarization separation, at short wavelengths which are used only for excitation and not for emission. The PBS designer can then sacrifice polarization purity in the UV range, and seek only high reflection. Such UV light reflected from the sample is not removed from the beam by the PBS, as would normally be the case in utilizing the present invention, but may instead be accommodated by placing a UV cut-on glass filter as the first element in the imaging optics. Suitable PBS units operable in the UV range may by way of example be obtained from Karl Lambrecht of Chicago, Ill. For systems which image only visible emissions, one suitable glass filter is GG-400 from Schott (Duryea, Pa.). This cut-on filter must have a high transmission at all wavelengths for which emissions are to be imaged, and the PBS must also exhibit at those wavelengths its normal properties of polarization selectivity.

The present invention is not limited to use in the visible wavelength range and, throughout this disclosure, the term light is intended to indicate and include optical radiation of the visible, ultraviolet, and infrared ranges. The inventive systems may be constructed in many ways, and its components may be assembled in various combinations and with such substitutions of materials, thicknesses, angles, components and other aspects as will be evident to those skilled in the art as embodying rather than deviating from the invention described herein.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A fluorescence imaging system for imaging radiation emitted by a sample to be imaged by the system through fluorescing of the sample in response to illumination of the sample by illuminating radiation, said system comprising:
   an illumination source operable for emitting a beam of optical illuminating radiation along a first optical path;
   a detector for receiving and imaging radiation emitted from a sample along a second optical path in response to illumination of the sample by the illuminating radiation;
   a polarizing beamsplitter for (1) receiving illuminating radiation from the illumination source along the first optical path and selectively redirecting only the illuminating radiation of a first polarization state to the second optical path for illuminating the sample with the redirected illumination radiation of the first polarization state so as to effect fluorescing of the sample and emission of radiation from the sample, and for (2) receiving emission radiation from the sample along the second optical path and selectively transmitting through the beamsplitter along the second optical path for receipt by said detector only the emission radiation from the sample having substantially a second polarization state orthogonal to the first polarization state; and,
   at least one additional polarizer disposed in at least one of the first and second optical paths, which preferentially reduces the proportion of excitation light incident upon the detector.

2. The system of claim 1, wherein said polarizing beamsplitter comprises a prism-type polarizing beamsplitter cube.

3. The system of claim 1, wherein said polarizing beamsplitter comprises a plate-type polarizing beamsplitter.

4. The system of claim 1, wherein said polarizing beamsplitter element comprises a reflective polarizing film.

5. The system of claim 1, wherein the said least one additional polarizer is located in the first optical path between the illumination source and the polarizing beamsplitter for selectively polarizing the illumination radiation for receipt by the beamsplitter in the first polarization state.

6. The system of claim 1, wherein the said least one additional polarizer is located in the second optical path between the detector and the polarizing beamsplitter for further polarizing the emission radiation transmitted by the beamsplitter.

7. The system of claim 1, further comprising an optical filter in the first optical path between the illumination source and the polarizing beamsplitter for transmitting optical radiation within a selected wavelength range.

8. The system of claim 7, wherein said optical filter comprises a tunable filter.

9. The system of claim 7, further comprising a fiber-optic element in the first optical path between the optical filter and the polarizing beamsplitter for transmitting optical radiation within a selected wavelength range.

10. The system of claim 1, further comprising a filter in the second optical path between the polarizing beamsplitter and the detector.

11. The system of claim 10, wherein said filter comprises a tunable filter.

12. The system of claim 1, further comprising spectrometer means for determining spectral content of the emitted radiation incident upon said detector.

13. The system of claim 12, wherein said spectrometer means comprises one of a diffraction grating, a Michelson interferometer, a Sagnac interferometer, and a Fabry-Perot interferometer.

14. The system of claim 1, further comprising at least one birefringent element disposed in the second optical path between the polarizing beamsplitter and the sample, which transmits the excitation beam substantially in one of its initial polarization state and the orthogonal polarization state.

15. The system of claim 14, wherein said at least one birefringent element comprises a liquid crystal element.

16. The system of claim 14, further comprising mechanical means for selectively moving said at least one birefringent element into and out of the second optical path.

17. The system of claim 14, further comprising means for sequentially illuminating the sample location in each of two substantially orthogonal polarization states.

18. The system of claim 14, further comprising means for sequentially imaging emission radiation in each of two substantially orthogonal polarization states.

19. The system of claim 14, wherein said at least one birefringent element comprises a plurality of birefringent elements and an optical polarization switch having a first setting at which said plural birefringent elements transmit radiation within a predetermined range of wavelengths without alteration of polarization state.

20. The system of claim 19, wherein said optical polarization switch has a second setting at which said plural birefringent elements convert radiation within a first selected wavelength range from an initial polarization state to a final polarization state orthogonal to the initial polarization state and transmit light within a second selected wavelength range without substantial alteration of polarization state.

21. The system of claim 1, further comprising a reflective polarizer element disposed in the first optical path between the illumination source and the polarizing beamsplitter.

22. The system of claim 21, further comprising means for directing radiation reflected by said reflective polarizing element back toward the reflective polarizing element.

23. The system of claim 22, further comprising conversion means disposed between said reflective polarizing element and the illumination source for converting at least a portion of the radiation reflected by said reflective polarizing element from an initial polarization state when reflected by the reflective polarizing element to a final polarization state orthogonal to the initial polarization state.

24. The system of claim 1, further comprising a twisted nematic liquid crystal cell disposed in the second optical path between the polarizing beamsplitter and the sample.

25. The system of claim 4, wherein the film comprises DBEF.

26. The system of claim 8, wherein the tunable filter comprises at least one of an acousto-optical tunable filter, a liquid crystal tunable filter, a surface plasmon filter, and a mechanical filter wheel.

27. The system of claim 11, wherein the tunable filter comprises at least one of an acousto-optical tunable filter, a liquid crystal tunable filter, a surface plasmon filter, and a mechanical filter wheel.

28. The system of claim 1 wherein the at least one additional polarizer is a linear polarizer.

* * * * *